(12) United States Patent
Richards-Kortum et al.

(10) Patent No.: US 6,370,422 B1
(45) Date of Patent: Apr. 9, 2002

(54) FIBER-OPTIC CONFOCAL IMAGING APPARATUS AND METHODS OF USE

(75) Inventors: Rebecca Richards-Kortum, Austin, TX (US); Colin L. Smithpeter, Albuquerque, NM (US); Brett S. Bowman, Palo Alto, TX (US); Michael R. Descour, Tucson, AZ (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/272,719

(22) Filed: Mar. 19, 1999

Related U.S. Application Data
(60) Provisional application No. 60/078,635, filed on Mar. 19, 1998.

(51) Int. Cl.[7] ................................................ A61B 6/00

(52) U.S. Cl. .................... 600/478; 600/182; 606/10

(58) Field of Search .............................. 600/473, 476, 600/478, 160, 176, 182; 359/366, 368; 606/3, 4, 10, 11, 14–17; 250/216, 227.26

(56) References Cited

U.S. PATENT DOCUMENTS

| | | | |
|---|---|---|---|
| 4,537,472 A | | 8/1985 | Asoma ........................ 350/415 |
| 4,938,205 A | | 7/1990 | Nudelman ...................... 128/6 |
| 5,120,953 A | * | 6/1992 | Harris ....................... 250/227.2 |
| 5,515,864 A | | 5/1996 | Zuckerman .................. 128/633 |
| 5,780,857 A | * | 7/1998 | Harju et al. .............. 250/458.1 |
| 5,785,651 A | | 7/1998 | Kuhn et al. .................. 600/310 |
| 5,785,704 A | | 7/1998 | Bille et al. ..................... 606/17 |
| 5,788,639 A | | 8/1998 | Zavislan et al. ............. 600/476 |
| 5,813,987 A | | 9/1998 | Modell et al. ............... 600/473 |
| 5,880,880 A | * | 3/1999 | Anderson et al. ............ 359/385 |
| 6,159,445 A | * | 12/2000 | Klaveness et al. ........... 424/9.6 |
| 6,210,401 B1 | * | 4/2001 | Lai .............................. 606/12 |

OTHER PUBLICATIONS

Bowman, "Optomechanical design of an endoscope for confocal microscopy," M.S. thesis, University of Texas at Austin, 1997.

Delaney and Harris, "Fiberoptics in confocal microscopy," In: Handbook of Biological Confocal Microscopy, J. Pawley, Ed,, Plenum, New York, NY, 2nd edition, chapter 33, pp. 515–523, 1995.

Delaney et al., "Fibre optic confocal imaging (FOCI) for subsurface microscopy of the colon in vivo ," J. Anatomy, 184:157–60, 1994.

Dickensheets and Kino, "A Scanned Optical Fiber Confocal Microscope," SPIE 2184:39–47, 1994.

Dunn et al., "Sources of Contrast in Confocal Reflectance Imaging", Appl. Optics, 35:3441–3446, 1996.

Giniunas et al., "Scanning fiber–optic microscope for microendoscopy with gradient index lenses probe," In: Optical Fibers in Medicine VIII., 1893: 90–92, 1993a.

Giniunas et al., "Endoscope with optical sectioning capability," Appl. Optics, 32(16):2888–90, 1993.

Gmitro and Aziz, "Confocal microscopy through a fiber optic imaging bundle," Optics Lett., 18(8):565–7, 1993.

Gu et al., "Image formation in a fiber–optical confocal scanning microscope," Optical Society of America, 8(11):1755–61, 1991.

Inoue, "Foundations of confocal scanned imaging in light microscopy," In: Handbook of Biological Confocal Microscopy, J. Pawley, Ed., Plenum, New York, NY, 2nd edition, pp. 1–17, 1995.

(List continued on next page.)

Primary Examiner—Marvin M. Lateef
Assistant Examiner—Shawna J. Shaw
(74) Attorney, Agent, or Firm—Fulbright & Jaworski

(57) ABSTRACT

An apparatus and methods for fiber optic confocal imaging systems. A plurality of fibers are in communication with a scan system that controllably deflects incident radiation into the fibers in a raster pattern. An index matching agent reduces specular reflections from the fibers.

41 Claims, 33 Drawing Sheets

OTHER PUBLICATIONS

Jester et al., "In vivo, real–time confocal imaging," *J. Electron Microscopy Tech.*, 18:50–60, 1991.

Kempe et al., "Comparative study of confocal and heterodyne microscopy for imaging through scattering media," *J. Optic. Soc. Am. A*, 13(1):46–52, 1996.

Kimura and Wilson, "Confocal scanning optical microscope using single mode fiber for signal detection," *Appl. Optics*, 30(16):2143–50, 1991.

Leuing et al., "Fluorescence imaging and spectroscopy of 5–aminolevulinic acid induced protoporphyirn IX for the detection of neoplastic lesion in the oral cavity," *Am. J. Surg.*, 172:674–77, 1996.

Liu et al., "Dependence of tissue optical properties on solute–induced changes in refractive index and osmolarity" *J. Biomed. Optics*, 1:200–211, 1996.

Mahadevan–Jansen and Richards–Kortum, Raman spectroscopy for the detection of cancers and pre–cancers (review), *J. Biomed. Opt*, 1:31–70, 1996.

Masters and Thaer, "Real–time scanning slit confocal microscopy of the in vivo human cornea," *Appl. Optics*, 33(4):695–701, 1994.

Petroll et al., "Three–dimensional imaging of corneal cells using in vivo confocal microscopy," *J. Micros.*, 170(3):213–219, 1993.

Rajadhyaksha et al., "In vivo confocal scanning laser microscopy of human skin: melanin provides strong contrast", *J. Invest. Dermatol.*, 104(6):946–62, 1996.

Ramanujam et al., "Development of a multivariate statistical algorithm to analyze human cervical tissue fluorescence acquired in vivo, "*Lasers Surg. Med.*, 19(1):46–62, 1996.

Ramanujam et al., "In vivo diagnosis of cervical intraepithelial neoplasia using 337–nm–excited laser induced fluorescence," *In: Proc. Nat. Acad. Sci. USA*, 91:10193–97, 1994.

Ramanujam et al., "Fluorescence Spectroscopy: A diagnostic tool for cervical epithelial neoplasia (CIN)" *Gynecol. Oncol.*, 52:31–38, 1994.

Richards–Kortum et al., "Spectroscopic diagnosis of colonic dysplasia," *Photochem. Photobiol.*, 53(6):777–786, 1991.

Richards–Kortum et al., "Description and Performance of a fiber optic confocal fluorescence spectrometer," *Appl. Spectroscopy*, 48(3):350–355, 1994.

* cited by examiner (a)  (b)

FIBER-OPTIC CONFOCAL IMAGING APPARATUS AND METHODS OF USE

This application claims priority to provisional patent application Ser. No. 60/078,635 filed Mar. 19, 1998, entitled, "Fiber-Optic Confocal Imaging Apparatus and Methods of Use" by Richards-Kortum et al. The entire text of the above-referenced disclosure is specifically incorporated by reference herein without disclaimer.

The United States government has rights in the present invention pursuant to grant number 1R01 CA73920 from the National Institutes of Health.

BACKGROUND OF THE INVENTION

1. Field of the Invention

The present invention relates generally to the fields of optics and microscopy. More particularly, it concerns apparatus and methods for analyzing samples using fiber-optic confocal imaging techniques.

2. Description of Related Art

Currently, two methods are available for imaging at the cellular level in the body: Optical Coherence Tomography (OCT) (Izatt et al., 1994; Huang et al., 1991; Schmitt et al., 1993; Yadlowsky et al., 1995; Swanson et al., 1993; Schmitt et al., 1994) and confocal imaging (Petroll et al., 1993; Jester et al., 1991; Rajadhyaksha et al., 1995a; Gmitro and Aziz, 1993; Massig et al., 1994; Masters and Thaer, 1994; Giniunas et al., 1993a; 1993b; Delaney et al., 1994).

OCT uses interference techniques with low-coherence light sources to select the light coming from a distinct depth (Huang et al., 1991). The basic system uses a Michaelson interferometer with the tissue sample in one arm and a reference mirror in another arm. When the reflections from both arms are combined at the detector, an interference maximum or minimum is detected when the reflections from both arms are matched in optical path length (time-of-flight). The strength of the interference is proportional to the amount of light reflected from the corresponding optical path length within the tissue. The temporal frequency of the interference maximum and minimum can be modulated by translating the reference mirror at a constant velocity or by stretching the path length in the reference arm with a piezo-electric transducer at the modulation frequency. These systems use heterodyne detection of the modulated interference signal to detect as little as $5 \times 10^{-10}$ of the incident light (Huang et al., 1991). The axial resolution of OCT depends on the coherence length of the illumination source, which is in the range of 10 to 20 $\mu$m (Swanson et al., 1993) for semi-conductor sources. More recent work with mode-locked Ti:Sapphire and Forrestrite lasers have yielded coherence lengths as small as 1.8 $\mu$m (SPIE Proceedings, 1997). The lateral resolution is determined by the diffraction-limited spot size in the tissue.

OCT forms a cross-sectional image of the tissue by mapping the intensity of the reflected light as the sampling point is translated in the axial and lateral dimensions. The sampling point is moved in depth by the translation of the reference mirror. The lateral dimension is achieved by translation of the optics over the surface of the tissue. Much of the in vivo imaging done with OCT has been in the eye (Swanson et al., 1993). Some researchers have also attempted to use the technique to image scattering tissue such as human skin, however, have not obtained images of individual cells due to the lack of spatial resolution (Yadlowsky et al., 1995). Thus, while OCT has a high sensitivity, it has not demonstrated the spatial resolution necessary to image cellular structure. Although the new mode-locked laser gives OCT the potential to achieve the desired resolution, the cost and complexity of these lasers make them impractical for clinical use.

The first attempts at in vivo confocal imaging have been done with a modified scanning Nipow disk microscope (Petroll et al., 1993; Jester et al., 1991). A Nipow disk refers to fiat disk which has a staggered array of pinhole apertures spread over the entire disk. At one instant in time, one of the apertures passes the illumination light and detects the reflected confocal light. As the disk spins, the aperture being used for illumination and detection moves around the disk, thereby, imaging the entire sample. The disks can spin at very high speeds to produce images at video rates. These systems have been used to image in vivo cornea and several organs of a rat which had been exposed by laparotomy. The best spatial resolution reported to date is approximately 7 $\mu$m, with no mention of the sensitivity or corresponding maximum penetration depth. One limitation of this apparatus is the fact that these microscopes are susceptible to misalignment of the disk.

More recently, a confocal system has been developed with a spatial resolution sufficient to image individual skin cells in a living human (Rajadhyaksha et al., 1995b). The instrument is a simplified confocal microscope with a standard pinhole aperture and scanning mirrors. A high numerical aperture (NA) oil-immersion objective lens is used in contact with the skin to achieve a lateral resolution of approximately 2 $\mu$m. No values have been reported for the sensitivity of the system, however it is capable of imaging the entire thickness of the forearm epithelium and into the rete ridges of the underlying stroma using 830 nm light. Images of cell size and nuclear to cytoplasmic ratio obtained with this system agree well with those measured from biopsies, validating the concept that in vivo confocal imaging can be used to assess tissue morphology. However, the size and configuration of illumination optics prevents use of this system to image tissues within moderately accessible cavities such as the cervix or mouth.

Several authors have proposed fiber optic systems for in vivo confocal imaging (Massig et al., 1994; Masters and Thaer, 1994; Giniunas et al., 1993a; Giniunas et al., 1993b; Delaney et al., 1994) based upon fiber optics. These designs implement confocal detection through a single fiber optic. These designs also incorporate some method of translating the endpiece optics in the axial and transverse directions to form an image. Designing an endoscopic system encompassing a miniature, high speed mechanical scanning system with high spatial resolution is difficult.

Another approach to a fiber optic design (Gmitro and Aziz, 1993) uses a fiber optic imaging bundle as a confocal image conduit between the endpiece optics and a confocal microscope. The function of the confocal microscope was to scan the illumination spot across the fiber bundle and to detect the emerging light. This arrangement does avoid the need for a mechanical translation system in the endpiece, however a commercial confocal microscope is expensive and cumbersome, limiting its usefulness as a practical clinical tool. In addition, the high absorption and scattering of the tissue will not allow the fluorescence excitation and emission light to penetrate the entire depth of the epithelium.

More recently, the same design has been implemented for reflection imaging using white light (Juskaitis et al., 1997) Reflection imaging is capable of penetrating to greater depths; however, the use of a white light source will limit the illumination power available to the system. A consequence of the limited illumination power will be a limited penetration depth due to loss of signal in scattering tissue. The rationale given for using white light is eliminating the speckle observed when imaging a resolution test target with laser light.

Although the potential of both in vivo confocal imaging with subcellular resolution and of fiber optic confocal imaging has been demonstrated, there is currently not a system which provides the imaging capabilities required for imaging tissues in vivo within the physical constraints necessary to achieve sufficient resolution and magnification of tissues within a living organism.

The system described by Juskaitis et al. (1997) uses a combination of angle polishing and index matching with glycerin to "prevent" specular reflection from the faces of the fiber bundle. Because the fiber bundle requires a difference in index between the individual fiber cores and cladding to function, it is not possible to eliminate or "prevent" the reflection from the fiber face at the proximal end (i.e. the end that light is injected into). Instead, the reflections can be minimized by using a matching oil with an index half way between the index of the cores and the cladding. Indeed, Juskaitis et al. use such an oil. While it is theoretically possible to eliminate the reflections from the distal end by using an oil with an index exactly equal to the index of the fiber cores, it is not practically feasible due to manufacturing limitations and variations.

If the laser has a coherence length greater than the separation between either fiber face and the image plane, the reflections from the fiber faces will interfere with the light reflected from the image plane. The argon laser used by Juskaitis et al. has a coherent length of several meters. It is likely that the length of fiber bundle used was less than two meters. Thus, the unstable speckle pattern they report is a result of interference between one, or both, of the reflections from the fiber faces and the light from the image plane. The selection criteria of the laser of the present invention is a coherence length less than the separation between the distal end of the fiber and the image plane to avoid this problem.

A scanned optical fiber confocal microscope is described by Deckensheets and Kino (1994). However, the fresnel objective lens used in this microscope was not able to achieve the high NA needed for imaging cellular structure.

U.S. Pat. No. 5,659,642, describes a confocal microscope and endoscope similar to that of the present invention. However, unlike the present invention, this microscope lacks a method for controlling the specular reflections from the faces of the fiber bundle.

SUMMARY OF THE INVENTION

The present invention overcomes these and other limitations in the prior art by providing apparatus comprising a confocal fiber optic imaging system. In one embodiment, the device has been shown to achieve the resolution and imaging necessary in vivo to permit the detection and diagnosis of precancerous lesions in tissues such as those involving the epithelium. The apparatus disclosed provide clinical tools which dramatically improve recognition and monitoring of biological specimens such as epithelial pre-cancers of the oral mucosa, uterine cervix, urinary bladder, colon, as well as other organs with high incidence of epithelial cancer. The apparatus has produced images of physiological structure with micron resolution at 15 frames per second. Moreover, a series of lenses designed and constructed to incorporate the fiber optic bundle directly into the imaging system was developed to overcome the specular reflections from the face of the fiber optic bundle.

In one sense, the invention encompasses the design and development of a fiber optic confocal imaging system which uses reflected light to produce images of tissue with several micron resolution. This system provides the user with images of the cellular structure and organization of the sampled tissue. This information can be used to determine the morphology of tissue and its potential for diseases such as cancer.

A confocal optical system places an aperture in a conjugate image plane to reject any light which is not reflected from the focus of the optical system (Inoue, 1995). The confocal technique of selecting only the light reflected from the focal plane is sometimes referred to as optical sectioning.

The present invention provides a fiber optic confocal microscope which comprises a plurality of optical fibers packed side by side in a bundle to form a characteristic image of the sample at the focal plane from the reflected illumination light in real time. The apparatus utilizes index matching to detect the sample reflection of biological sample.

The apparatus may quantitatively analyze a variety of samples, including biological samples. A confocal reflectometer according to the present disclosure may measure the reflected light from a single point. A reflectometer built in accordance with the present disclosure has demonstrated resolution near the diffraction limit and the sensitivity to detect a 0.05 refractive index mismatch under 3 optical depths of scattering.

Lenses to incorporate a fiber bundle into a confocal microscope were designed and assembled. An apparatus according to the present disclosure has shown that specular reflection from fiber optic bundle faces may be controlled, and lateral resolution in the range of approximately 5 $\mu$m may be achieved. Likewise, an axial resolution of approximately 15 $\mu$m has been obtained using the disclosed apparatus.

In one aspect, the invention is a confocal imaging apparatus for analyzing a sample including a radiation source, a scan system, a scan lens, a plurality of fibers, a distal index matching agent, a coupling lens, and a detector. The radiation source is configured to emit incident radiation. The scan system is in optical communication with the radiation source and is configured to controllably deflect the incident radiation. The scan lens is in optical communication with the scan system and is configured to focus the incident radiation. The plurality of fibers have a proximate end and a distal end. The proximate end is in optical communication with the scan lens and is configured to receive the incident radiation focused from the scan lens. The distal index matching agent is coupled to the distal end and is configured to reduce specular reflection from the plurality of fibers. The coupling lens is in optical communication with the distal end and is configured to focus the incident radiation toward the sample to produce secondary radiation from the sample. The detector is in optical communication with the scan system and is configured to receive at least a portion of the secondary radiation and to produce a signal corresponding therewith.

In other aspects, the incident radiation may include near infrared radiation. The radiation source may be a Ti:Sapphire laser. The radiation source may be a diode pumped Nd:YAG laser. The scan system may include a pair of orthogonal galvanometers. The scan system may include a spinning polygon. The scan system and the scan lens may be adapted to illuminate a single fiber of the plurality of fibers. The apparatus may also include a proximal polarizing agent in operative relation to the proximal end and configured to reduce specular reflection from the plurality of fibers. The apparatus may also include a depth translation system in operative relation with the plurality of fibers. The depth translation may include a translation stage. The depth translation system may include a suction agent. The suction agent may include a tube having a plurality of channels, and at least one of the channels may be adapted to deliver saline while at least another one of the channels may be adapted for suction. The centers of the plurality of fibers may be separated by about 5 microns. At least one of the plurality of fibers may include a core and a cladding, and the distal index matching agent may include a fluid having an index of refraction substantially equal to an index of refraction of the core. The apparatus may also include a beam splitter in optical communication with the radiation source and the detector. The, beam splitter may include a wedge angle. The scan system may be configured to controllably deflect the incident radiation in a raster pattern. The apparatus may also include an aperture positioned between the coupling lens and the detector. One of the plurality of fibers may be an illuminated fiber transporting the secondary radiation toward the detector, and the aperture may have a diameter adapted to block at least a portion of the secondary radiation emanating from a proximate end of one or more fibers adjacent the illuminated fiber. The apparatus may also include a controller coupled to the scan system and to the detector. The apparatus may also include control electronics and a video card coupled to the controller. The control electronics may be adapted to provide one or more timing signals to the video card. The apparatus may also include an objective in optical communication with the coupling lens, and a magnification of the coupling lens may be adapted to fill the objective with the incident radiation. The apparatus may have a lateral resolution of about 5 microns.

In another respect, the invention is a confocal imaging apparatus for analyzing a sample and includes a laser, a scan system, a scan lens, a plurality of fibers, a proximal index matching agent, a distal index matching agent, a coupling lens, and a detector. The laser is configured to emit incident radiation. The scan system is in optical communication with the laser and is configured to controllably deflect the incident radiation in a raster pattern. The scan lens is in optical communication with the scan system and is configured to focus the incident radiation in the raster pattern. The plurality of fibers have a proximate end and a distal end. The proximate end is in optical communication with the scan lens and is configured to receive the incident radiation focused from the scan lens in the raster pattern. The proximal index matching agent is coupled to the proximate end and is configured to reduce specular reflection from the plurality of fibers. The distal index matching agent is coupled to the distal end and is configured to reduce specular reflection from the plurality of fibers. The coupling lens is in optical communication with the distal end and is configured to focus the incident radiation in the raster pattern toward the sample to produce secondary radiation from the sample. The detector is in optical communication with the scan system and is configured to receive at least a portion of the secondary radiation and to produce a signal corresponding therewith.

In other aspects, at least one of the plurality of fibers may include a core and a cladding, and the distal index matching agent may include a fluid having an index of refraction substantially equal to an index of refraction of the core. At least one of the plurality of fibers may include a core and a cladding, and the proximal index matching agent may include a fluid having an index of refraction between an index of refraction of the core and an index of refraction of the cladding. The fluid may have an index of refraction of about halfway between the index of refraction of the core and the index of refraction of the cladding. The apparatus may also include a depth translation system in operative relation with the plurality of fibers. The depth translation system may include a translation stage. The depth translation system may include a suction agent. The apparatus may also include a controller coupled to the scan system and to the detector.

In another respect, the invention is an endoscopic confocal imaging apparatus for in vivo analysis of a sample, including a confocal system and an endoscope. The confocal system includes a radiation source, a scan system, a scan lens, a plurality of fibers, and a detector. The radiation source is configured to emit incident radiation. The scan system is in optical communication with the laser and is configured to controllably deflect the incident radiation. The scan lens is in optical communication with the scan system and is configured to focus the incident radiation. The plurality of fibers have a proximate end and a distal end. The proximate end is in optical communication with the scan lens and is configured to receive the incident radiation focused from the scan lens. The detector is in optical communication with the scan system. The endoscope includes a distal index matching fluid reservoir, a coupling lens, and an endoscopic tube. The distal index matching fluid reservoir is configured to sealably contain a distal index matching fluid. The reservoir is coupled to the distal end, and the fluid is configured to reduce specular reflection from the plurality of fibers. The coupling lens is in optical communication with the distal end and is configured to focus the incident radiation toward the sample to produce secondary radiation from the sample detectable by the detector to produce a signal corresponding therewith. The endoscopic tube is configured to house the distal end, the reservoir, and the coupling lens.

In other aspects, the apparatus may also include an objective in optical communication with the coupling lens. A magnification of the coupling lens may be adapted to fill the objective with the incident radiation. The apparatus may also include a fiber shield configured to house and protect at least a portion of the plurality of fibers. The scan system may be configured to controllably deflect the incident radiation in a raster pattern. The apparatus may also include a suction hood coupled to the endoscope. The apparatus may also include a controller coupled to the scan system and to the detector.

In another respect, the invention is a method for confocal imaging of a sample. Incident radiation is emitted from a radiation source. Incident radiation is controllably deflected with a scan system in optical communication with the radiation source. Incident radiation is focused with a scan lens in optical communication with the scan system. The incident radiation focused from the scan lens is received with a proximate end of a plurality of fibers, the proximate end being in optical communication with the scan lens. Specular reflection from the plurality of fibers is reduced with a distal index matching agent coupled to a distal end of the plurality of fibers. The incident radiation is focused toward the sample to produce secondary radiation from the sample with a coupling lens in optical communication with the distal end. The secondary radiation focused from the coupling lens is received with the distal end. The secondary radiation is focused through the scan system with the scan lens. At least a portion of the secondary radiation is detected with a detector in optical communication with the scan system. A signal corresponding to the secondary radiation detected by the detector is produced to image the sample.

In other aspects, the coupling lens, the distal end, and the distal index matching agent may make up an endoscope, and the imaging of the sample may include in vivo endoscopic imaging of the sample. The controllably deflecting of the incident radiation may include deflecting the incident radiation in a raster pattern. The method may also include reducing specular reflection from the plurality of fibers with a proximal index matching agent coupled to a proximal end of the plurality of fibers. The sample may include biological tissue. The sample may include an integrated circuit wafer, or portion thereof. The method may also include enhancing contrast of the sample with a contrast agent. The contrast agent may include 5-aminolevulinic acid. The contrast agent may include acetic acid. The acetic acid may consist of about 6% acetic acid. The method may also include modifying a focus depth with a depth translation system in operative relation with the plurality of fibers. The depth translation system may include a suction agent configured to displace at least a portion of the sample by suction. The depth translation system may include a translation stage. The imaging may include cross sectional imaging.

BRIEF DESCRIPTION OF THE DRAWINGS

The following drawings form part of the present specification and are included to further demonstrate certain aspects of the present invention. The invention may be better understood by reference to one or more of these drawings, in which like reference numerals have been applied to like elements, in combination with the detailed description of specific embodiments presented herein.

DESCRIPTION OF ILLUSTRATIVE EMBODIMENTS

The presently disclosed methods and apparatus may be applied to the imaging of essentially sample, including any tissue in human or other animal. Such tissues include bone, muscle, ligament, tendon, cartilage, heart, mucus membrane, intestine, gall bladder, pancreas, urethra, lung, brain, prostate, kidney, liver, ovary, breast, skin, stomach, esophagus, head & neck, testicles, colon, cervix, lymphatic system and blood.

The presently disclosed methods and apparatus may be applied to the measurement of tumor resection margins. Tumors may be of essentially any origin and include cancers of the lung, brain, prostate, kidney, liver, ovary, breast, skin, stomach, esophagus, head and neck, testicle, colon, cervix, lymphatic system and/or blood. The presently disclosed methods and apparatus may be of particular use in the field of forensic medicine. In particular, microscopic, 3-dimensional images of wounds may be created. The presently disclosed methods and apparatus may be used in the resection of animal tumors to assess if removal of such tumors was complete. The apparatus disclosed herein may also be used to determine the efficacy of drug therapy in an animal model. Presently, to address the effectiveness of a cancer drug in an animal model, the animals are sacrificed at regular intervals to examine the cancerous cells. Using the disclosed apparatus, one may examine the cancerous tissues of the animals without having to sacrifice the animal or disturb the tissue. The presently disclosed methods and apparatus may be used to image particles in a flow or slurry for distribution and form. The probe may be immersed into the product to image various depths. Additionally, a portable system may be used at multiple stations. The presently disclosed methods and apparatus may also be used to inspect semiconductor devices, including but not limited to, IC wafers or portions thereof.

Figure 1:
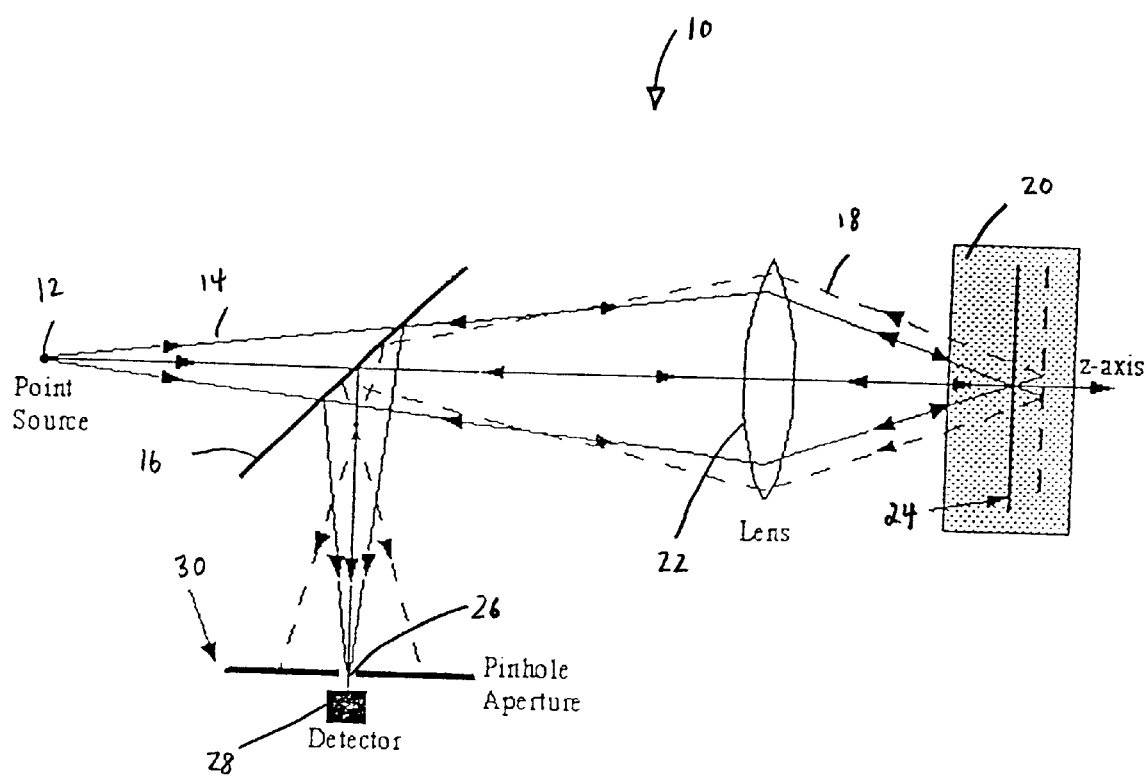
FIG. 1. is a schematic diagram of optical sectioning property of confocal imaging.

FIG. 1 illustrates the optical sectioning principle of confocal imaging. This schematic represents the different pathways of light reflected from a sample illuminated by a point light source 12. The illumination light, or incident radiation 14, passes through a beam splitter 16 and is focused by a lens 22 to a point within the sample 20, which may be tissue. Since tissue is highly scattering, some of the illumination light 14 is reflected from all points illuminated within the sample 20. The light rays 18 reflected from the focal region of the lens may be refocused by the lens 22 and partially reflected by the beam splitter 16 to a point at the conjugate image plane. If a small pinhole aperture 26 is centered on the focused beam in the conjugate image plane, a majority of the light returning from the focal region in the tissue is passed to the detector 28. Light reflected from depths greater than the focus region (dashed line) comes to a focus in front of the pinhole plane 30. This light is diverging and spread out when it reaches the pinhole so its intensity is significantly reduced by the aperture. Similar rejection occurs for light coming from depths less than the focal region. Optical sectioning is accomplished for lateral points as well since light returning from these points is imaged lateral to the pinhole. Thus the confocal system is able to isolate light returning from a finite volume, without the need for physical sectioning. Scanning the focal spot in the axial and radial dimensions forms a map, or image, of the reflectance values from the focal region of each point in the sample.

Figure 2:
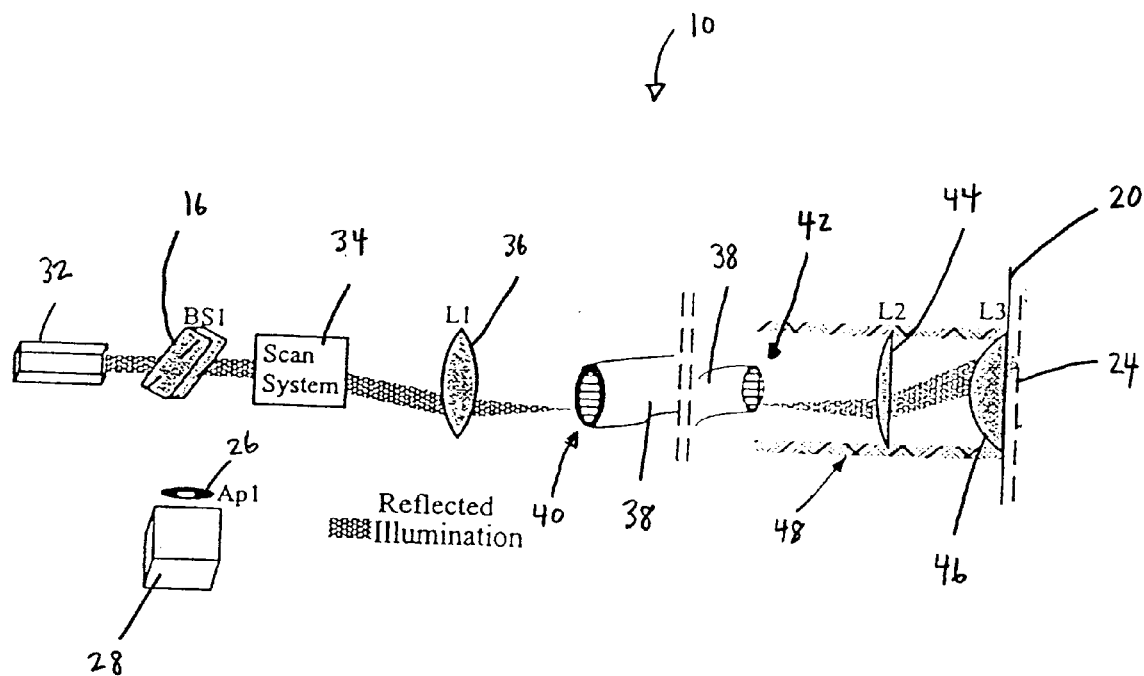
FIG. 2. is a diagram of one embodiment of a confocal fiber optic imaging system.

One embodiment of a confocal imaging apparatus 10 is depicted in FIG. 2. In this embodiment, apparatus 10 includes a radiation source 32, a beam splitter 16, an aperture 26, a detector 28, a scan system 34, a scan lens 36, a plurality of fibers (or, fiber bundle) 38, a coupling lens 44, an endpiece 48, an objective 46, a sample 20, and an imaging plane 24. Fiber bundle 38 has a proximate end 40 and a distal end 42.

In this embodiment, radiation from source 32 passes though a 50/50 beamsplitter (BS) 16 to a scan system 34. In one embodiment, scan system 34 may comprise two mirrors mounted on orthogonal galvanometers. In one embodiment, a monochromatic laser illumination source may be used as radiation source 32 and may provide adequate optical power and to avoid potential problems with chromatic aberrations. The function of scan system 34 is to deflect collimated radiation by an angle in the x-y plane. From the scanning mirrors the beam may be passed through scan lens 36 to a focus at proximate end 40 of fiber bundle 38. The fiber bundle 38 may consist of many small core diameter fibers, organized coherently in evenly spaced rows. The optics of scan lens 36 may be designed to produce a focused beam diameter less than a fiber diameter so that illumination light may enter only one fiber at any time. One galvanometer of scan system 34 may oscillate at high speeds in one axis to form a line scan across a row of fibers. A second galvanometer of scan system 34 may oscillate in the orthogonal axis at a much slower speed to move the line scan up and down the rows of fibers. As the two scanners oscillate the mirrors back and forth, the focused spot may moved across fiber bundle 38 in a raster pattern resulting in incident radiation from source 32 being coupled into every fiber of bundle 38 during a single page scan.

At distal end 42 of the fiber bundle 38, incident radiation emerging from the illuminated fiber may be imaged by a set of lenses (44 and 46) to a focal point within sample 20, which may be, in one embodiment, a tissue. The magnification of coupling lens 44 and objective 46 may determine the diameter of the focal waist within the sample, and thus the spatial resolution of the system. Because a sample such as tissue may be highly scattering, some of the incident radiation may be reflected, or backscattered, from all points illuminated. However, the photons backscattered from the focal region may be preferentially imaged back into the illuminated fiber. At the proximal end 40 of the fiber bundle 38, the confocal reflected light, the secondary radiation, emerging from the illuminated fiber may be collimated by scan lens 36 and de-scanned by scanning mirrors of scan system 34. After passing through scanning mirrors of scan system 34, 50% of the confocal light may be reflected from the beam splitter 16 onto detector 28. Aperture 26 may be placed in front of detector 28 with a diameter equal to the size of the fiber image in the back focal plane to block the reflected light from fibers adjacent to the illuminated fiber. As scanning mirrors of scan system 34 illuminate each fiber in the bundle 38, the secondary radiation from each fiber is detected, and a signal is produced corresponding to the detected radiation. That signal may then be analyzed and processed as is known in the art to form an analysis, such as an image, of sample 20. In one embodiment, a resulting image may be a map of the reflectance values from the focal plane in the tissue. In another embodiment, a map may be formed from fluorescence data gathered according to the above description.

When it is desirable to produce an image which is approximately parallel with the observed tissue surface, a method to manipulate the depth of the image plane in the tissue must be designed. At least two methods may be used for this purpose. In one embodiment, a suction agent may be used to displace at least a portion of sample 20 so that image plane 24 corresponds to a different depth of sample 20. In one embodiment, a suction cup may be positioned near the distal end 42 of a probe, adjacent sample 20. At the center of the probe the optics may be mounted in an aluminum housing. In one embodiment, surrounding the metal housing may be a plastic PFTE tube with four channels embedded within its wall. Two of these channels may be used to deliver saline and the other two for suction. A piece of rigid plastic tubing may be mounted over the PFTE at the distal end of the endpiece to form a suction cup. As suction is applied to the cup, the sample 20, which may be tissue, is pulled into the volume of the cup where the focal plane lies. By increasing or decreasing the amount of suction, a user may move the focal plane through the cell layers. A secondary advantage of using the suction device is minimizing motion artifact by attaching the probe to the tissue. Because the anticipated maximum displacement of ~0.5 µm is small compared to the anticipated diameter of the probe (5 to 25 mm), the physical distortion of the cells may be minimal.

In another embodiment, a translation system based upon piezo electric crystal rings may be employed. Three interconnected piezoelectric crystals may be placed between an inner stage, containing the fiber bundle 38 and optics assembly, and the outer casing of the probe. The outer two rings expand and contract radially in response to an applied voltage, while the center crystal expands and contracts along the axis of the probe. By appropriately adjusting the cycle of applied voltages to the three rings, controlled motion of the inner shaft relative to the outer shaft can be produced in a manner analogous to an inchworm drive. Such translation systems are commercially available (Inchworm, Burleigh Instruments Inc., Fishers, N.Y.) at diameters under 1 cm. The distance per cycle is proportional to the voltage applied and can be varied between several hundred nanometers and 8 µm.

To produce a cross-sectional image of tissue using one embodiment, a single line of fibers in bundle 38 may be scanned repeatedly, with the depth of focus advanced between each line scan. The speed of the translation system may be sufficient, in one embodiment, to advance the depth of focus at 8 kHz, the intended line scan frequency, in 1 µm steps, resulting in cross sectional images to depth of 512 µm at half video rate.

Another embodiment of the system is a variable opticalpower element located at the aperture stop of the confocalmicroscope objective 46. The aperture stop is located at the rear focal plane of the objective 46 (this makes the objective telecentric in object space). If an optical element is located at a focal plane of another optical element, the total power of the combination remains unchanged. What changes is the location of a principal plane. Principal planes are used in compound optical systems, such as microscope objectives, as reference planes for object and image distances. The introduction of a variable-power element in the rear focal plane of the microscope objective may provide a lever to translate the front principal plane. The location of the rear principal plane remains fixed. By changing the power of the additional optical element, one may translate the front principal plane and with it the location of the object plane. Such an embodiment is very similar to principles underlying the corrective effect of glasses. Specifically, eye-glasses are located in the front focal plane of the eye. No change in power results (thus no change in magnification) but correction is achieved via movement of the rear principal plane toward the retina, in the case of myopia correction.

One embodiment of a variable-power element may include an inflatable lens element (not shown), filled with water or a higher index fluid. One side of the element may be fixed, e.g., plane. The other side of the element may be a flexible membrane, either containing the fluid or air in the case of fluid on the outside of the lens.

Figure 3:
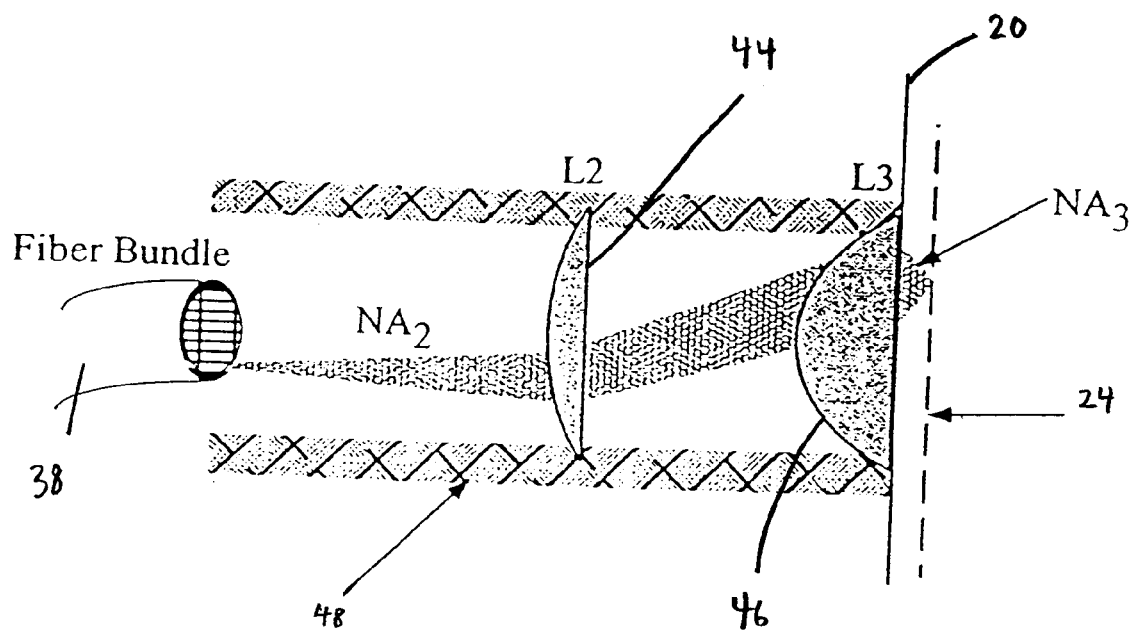
FIG. 3. is a functional diagram of optics within an endpiece to illustrate the magnification requirements according to one embodiment.

Lateral resolution may be determined by the geometrical magnification of endpiece optics, including coupling lens 44 and objective 46. In one embodiment, the separation between fibers in bundle 38 may be about equal to the diameter of each fiber. For the endpiece arrangement shown in FIG. 3, the magnification is equal to the ratio of the NA in the object plane to the NA at the fiber bundle 38. The separation between fiber images, D, in the sample 20 may be determined by the magnification, M as:

$$D = FM = F\frac{NA_2}{NA_3}.$$

where F is the separation between the fibers in the bundle 38. The minimum magnification of the endpiece to place 2.4 of the fiber images within 3 µm is:

$$M = 3\ \mu m/2.4F$$

In one embodiment, the fiber separation in the bundle 38 is about 5 µm. Using this bundle 38 requires a demagnification of 0.25×between the fiber bundle 38 and the sample 20 to provide 3 µm resolution.

The last variable in the resolution equation are the actual values of $NA_2$ and $NA_3$. Requiring that the laser light be coupled into one fiber at a time determines the value of $NA_2$. To produce a beam waist of 5 µm at the face of the fiber, the light incident on the fiber from scan lens 36 must have an NA of 0.2. The light will exit the fiber bundle 38 with the same NA, so a demagnification of 0.25 results in $NA_3$ being at least 0.8. Objective lenses with a NA of 0.8 to 1.3 are commercially available.

The axial resolution of the system may be estimated from the background equations on fiber optic confocal systems and may be about 2.4 µm for $NA_3$ 0.8 and a 5 µm fiber.

In embodiments described herein, possible sources of energy loss in the system may include specular reflections from optical surfaces, absorption of the light by the components, and absorption or scattering of the light by the tissue. The losses due to absorption and scattering may be minimized by using illumination light in the near infrared (NIR) region (~800–1100 nm) of the optical spectrum. At these wavelengths the absorption coefficient is small compared to the scattering coefficient (Cheong et al., 1990) and is therefore negligible.

Using incident radiation in the NIR at ~800 nm, a suitable detector 28 may be silicon based (Webb and Hughes, 1993). Previous work in selecting detectors (Webb and Hughes, 1993) has shown that given a signal which is a small fraction of the input power and the sampling bandwidth of a typical imaging system (~10 MHz), an avalanche photodiode (APD) is required. A typical APD and amplifier combination (Hamamatsu C4560) has a minimum detectable signal of 1.6 mW for a S/N ratio of 2. As a result, detecting the minimum signal requires an input laser power of 195 mW to overcome the electronic noise of the detector and amplifier. This power is achievable with diode lasers and other solid state lasers in the NIR.

To achieve the acquisition of images at video rates, scan system 34 has to move the focused illumination light over every fiber optic in the bundle 38 approximately 30 times per second. Scan system 34 may be configured to deflect a collimated beam through a range of angles in the transverse plane. The deflection may be achieved by reflecting light from a mirror which is being rotated through a limited range of angles. It is also possible to deflect the beam by diffraction with an acousto-optic cell. For a 512×512 image, the line scan mirror must oscillate at 16 kHz to form 30 frames a second. The mirror moving the line scan through each frame requires an oscillation frequency of 30 Hz. Because galvanometers can easily achieve the 30 Hz and are relatively cheap, they may be used for the page scan mirror. The 16 kHz requirement on the line scan mirror may be met only by a resonant galvanometer or a spinning polygon.

A typical galvanometer is capable of oscillating at frequencies up to several hundred Hertz before friction and the momentum of the mirror make it unstable. To achieve higher frequencies there are specially designed galvanometers which oscillate at the mechanical resonance frequency of the shaft and mirror. Currently the maximum line scan frequency of a resonant galvanometer is 8 kHz which limits the video acquisition to 15 frames per second. Because it is a resonant device, the velocity of the 8 kHz galvanometer is sinusoidal. An effect of the sinusoidal velocity is a pixel temporal sampling frequency which varies sinusoidally within each line. Specifically, the sampling frequency varies between 7.5 MHz at the start of the line to 15 MHz in the center and back to 7.5 MHz by the end. Fortunately, the electronics to generate the video timing signals from the sinusoidal velocity have already been developed for the resonant galvanometer by one manufacturer, General Scanning. An additional concern is the fraction of time spent acquiring pixels, or duty cycle, in each page scan. A resonant galvanometer system acquires no pixels in the time it takes the mirror to move between the end of a line and the start of the next line, known as the flyback time, so the duty cycle of pixel acquisition is only 40%. In the resonant system, the page and line scan galvanometer are mechanically integrated into a single mount which makes the optical alignment straightforward.

Figure 4:
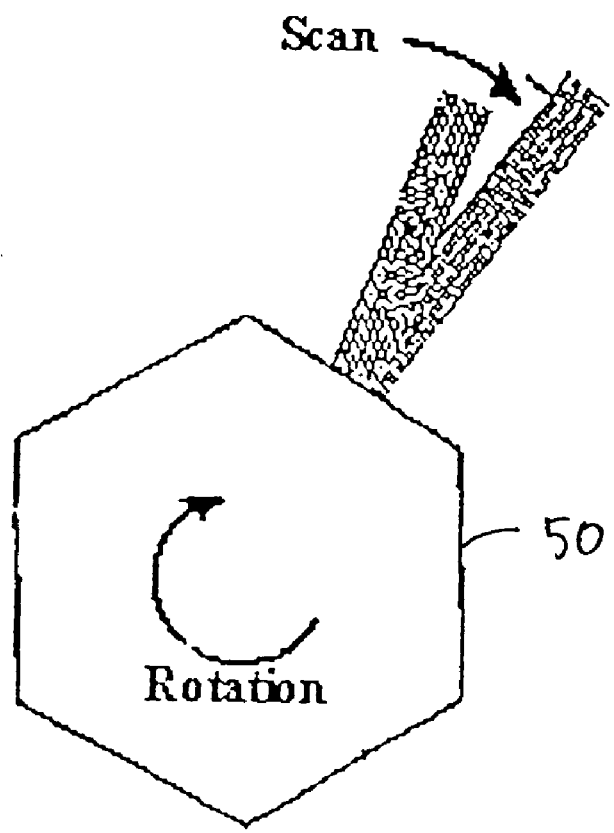
FIG. 4. is a schematic diagram of a polygon scanner according to one embodiment. As the polygon rotates the beam is scanned through a line.

In one embodiment, a polygon scanner shown in FIG. 4 may be used in scan system 34. As the polygon turns, the incident angle of the light to the mirrored facet increases and the beam scanned along a line until the end of the facet is reached, at which time another line scan begins with the next facet. Because the polygons can rotate at high RPM and there many facets in each rotation, the 16 kHz line scan rate is easily achieved. The duty cycle can be as high as 90% since there is no flyback time between lines.

Figure 5:
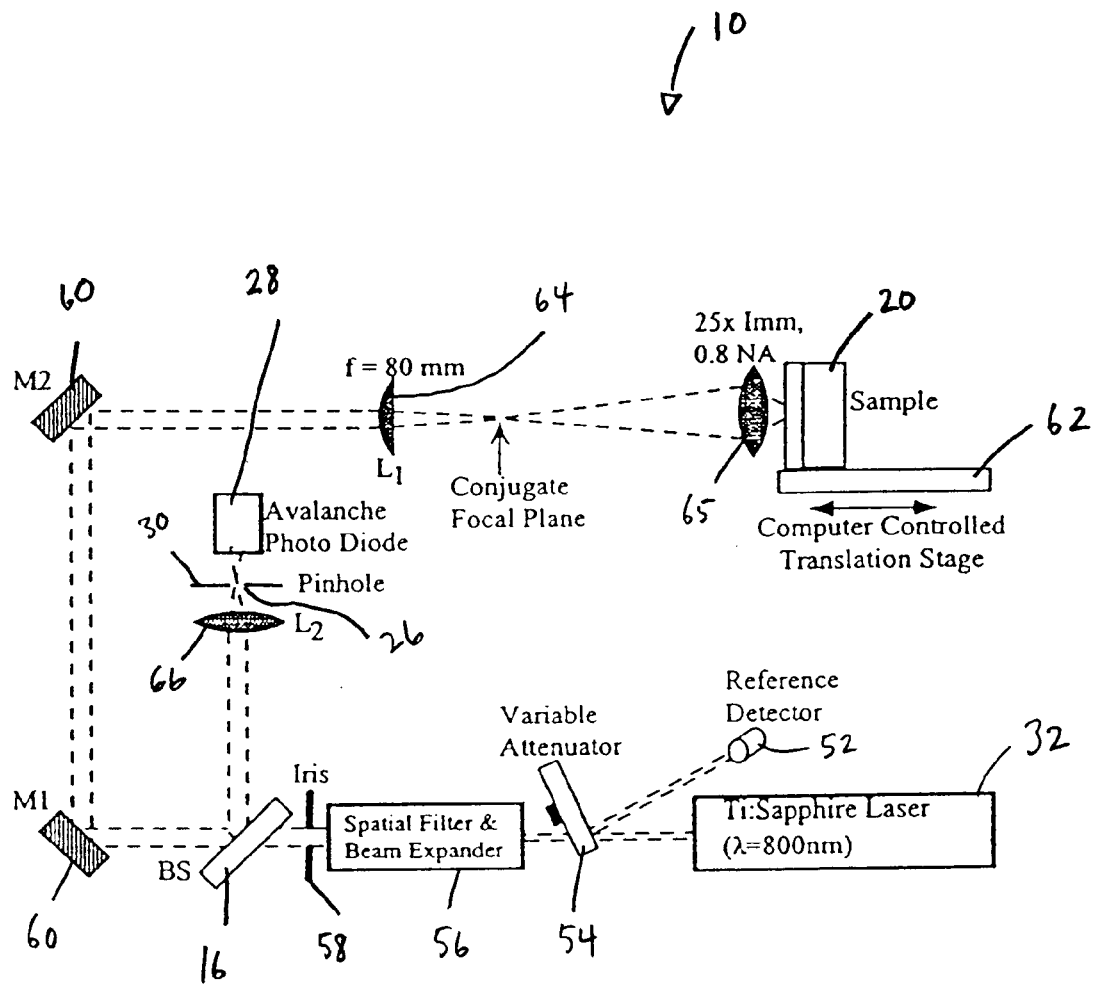
FIG. 5. show an experimental setup of one embodiment of a confocal reflectometer.

Turning to FIG. 5, there is shown a confocal imaging apparatus 10 according to one embodiment of the presently disclosed methods and apparatus. Apparatus 10 includes incident radiation source 32, reference detector 52, variable attenuator 54, filters and beam expanders 56, iris 58, beam splitter 16, mirrors 60, lens 66, pinhole 30, aperture 26, detector 28, lens 64, objective 65, sample 20, and translation stage 62.

In one embodiment, source 32 may lase in the fundamental transverse mode ($TEM_{00}$) only. In one embodiment, a Ti:Sapphire laser may be used, which may emit higher order modes. These higher order transverse modes may produce phase shifts across the wavefronts which may distort the focused beam.

In one embodiment, interference may be reduced if a source 32 with coherence length less than the minimum separation between the elements (~a few mm) is used. In the absence of interference, background signal may be subtracted or filtered out to restore the sensitivity. In one embodiment, a laser source 32 may lase with multiple longitudinal modes to produce a large spectral bandwidth and a corresponding short coherence length.

To avoid the misalignment, variable beam splitter/ attenuator 54 may be introduced into the beam path at an angle. The amount of light transmitted through the mirrored surface of the attenuator may be varied by rotating it. Such a method may provide a 40 dB range of laser power and stable alignment. The light reflected from the attenuator may be detected by a photodiode to monitor the laser power.

In one embodiment, using variable beam splitter 54 may cause wavefront distortion. A spatial filter 56 may be added to clean up the beam and restore the spatial resolution of the system. The spatial filter 56 may also be used as a beam expander to increase the diameter of the beam, in one embodiment, from approximately 1 mm to 6 min. Expanding the beam may reduce the refractive power needed in subsequent lenses, thereby reducing the spherical aberration.

Figure 6A:
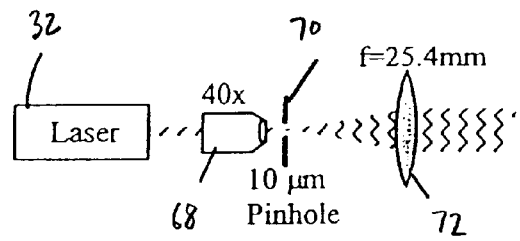
FIG. 6A. shows spatial filter/beam expanders used in one embodiment of a reflectometer.
Figure 6B:
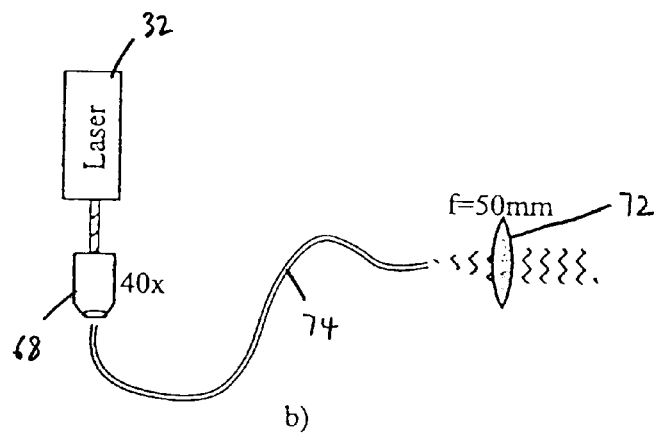
FIG. 6B. shows spatial filter/beam expanders used in one embodiment of a reflectometer.

Two forms of spatial filter/beam expander are shown in FIGS. 6A and 6B. The expanders show a source 32, an objective 68, a fiber 74, an aperture 70, and a lens 72. In FIG. 6A, the aperture may be about a 10 μm pinhole to match the $e^{-2}$ Gaussian beam waist so that only the fundamental spatial mode may be passed (Newport Research Corporation, 1993). Approximately 10% of the power may be lost going through the spatial filter. The ratio of the lens focal lengths may determine the expansion ratio. However, using this spatial filter it may be cumbersome to keep the laser aligned to the rest of the system due to the long path length between them. This problem may be solved by replacing the pinhole with a 830 nm single mode fiber as shown in FIG. 6B. If the position or angle of laser beam wanders, the power may be restored by adjusting the coupling of the laser to the fiber rather than the realigning the whole system. A consequence of using the fiber instead of the pinhole may be an increased power loss of approximately 20% through the spatial filter and a corresponding loss in sensitivity.

Iris 58 may be placed in the path of the collimated beam to control the diameter of the beam at the aperture of the objective. The diameter of the iris may be reduced until the diameter of the laser light and the objective match the diameter of the objective's aperture. In one embodiment, it may be critical to fill the aperture of the objective to maintain the spatial resolution (Keller, 1989). It may also be important not to introduce any excess light into the system to minimize specular reflections. The use of iris 58 meant that only the necessary light entered the system.

In one embodiment, beam splitter 16 may be designed to reflect 50% of the light in the near infrared (NIR) region of the spectrum. The side without the reflection coating may have an antireflection (AR) coating to reduce specular reflection. Even with the AR coating, a ghost reflection from the nonreflective side may be observed at the lens closest to the detection pinhole. A beam splitter 16 fabricated with a small angle between the two faces, a wedge angle, may be used to separate the ghost reflection from the signal light. Without the wedge angle, the sensitivity may have been reduced because this ghost reflection would be detected as a background signal.

The BS 16 may be placed in a mechanical mounting with X-Y tilt to facilitate the alignment of the signal light with the pinhole lens. It may be critical that a stable mount be used for the BS 16 since any movement of the BS 16 due to vibrations may cause movement of the focused light.

In the illustrated embodiment, three mirrors may be included in the system to make the sample arm vertical to the plane of the table. Only two of these mirrors 60 are shown in FIG. 5. Mirrors with a surface flatness of λ/10 may be used to minimize the distortion of the wavefronts.

Figure 7:
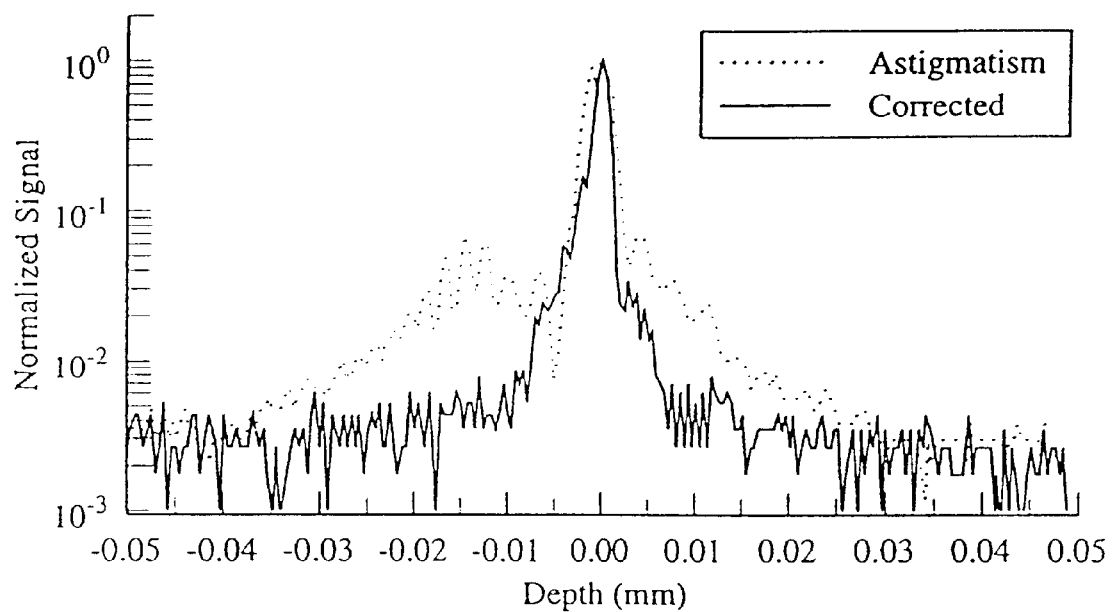
FIG. 7. shows the axial response of one embodiment of a reflectometer incorporating a mirror of unknown quality. A resolution scan from the system with a high quality mirror is included for comparison. A normalized pinhole radius of 3 was used for both scans.

FIG. 7 demonstrates the effects of aberrations created by a mirror of poor surface quality on the axial response of the reflectometer. The peak to the left of the central peak indicates mirror-induced astigmatism (Cogswell and Larkin, 1995) as well as spherical aberration. The response was measured by scanning the surface of microscope slide through the focus of the objective with water as the immersion medium. An axial scan from the corrected system with same dimensionless pinhole radius, $v_p$, is included for comparison.

Two of the mirrors 60 may be placed in X-Y tilt mechanical mountings. Together they may function as steering mirrors to adjust the lateral position and propagation angle of the light. The ability to manipulate the position and angle of the light was crucial to aligning the complete system.

In one embodiment, inherent spherical aberrations of lenses 64 and 66 may degrade the resolution of the system. Spherical aberration is proportional to the height of the ray from the optical axis and the optical power of each surface (Smith, 1990). As such, the spherical aberration of each lens may be minimized by aligning each normal to the incident light and distributing the refraction of the light between both surfaces.

Using lenses with multilayer AR coatings designed for the illumination wavelength may reduce the amount of specular reflections detected. This may be especially critical with the interference between the specular reflection light and the signal light.

To maintain the optical resolution when detecting signals within sample 20, it may be necessary to match the index of the medium between the objective and sample to the index of the sample. Spherical aberrations may be created by the refraction at the surface of the sample if the index of the medium was different from the index of the sample (Sheppard et al., 1994; Sheppard and Gu, 1992). An immersion objective with an index correction collar may be used to match the index.

In one embodiment, immersion objectives may be designed to work with a conjugate image 150 mm behind the shoulder of the objective 65. Because the aberrations of the objective may be well corrected for a 150 mm conjugate image, the focal plane of lens 64 may be placed at the 150 mm conjugate.

Figure 8:
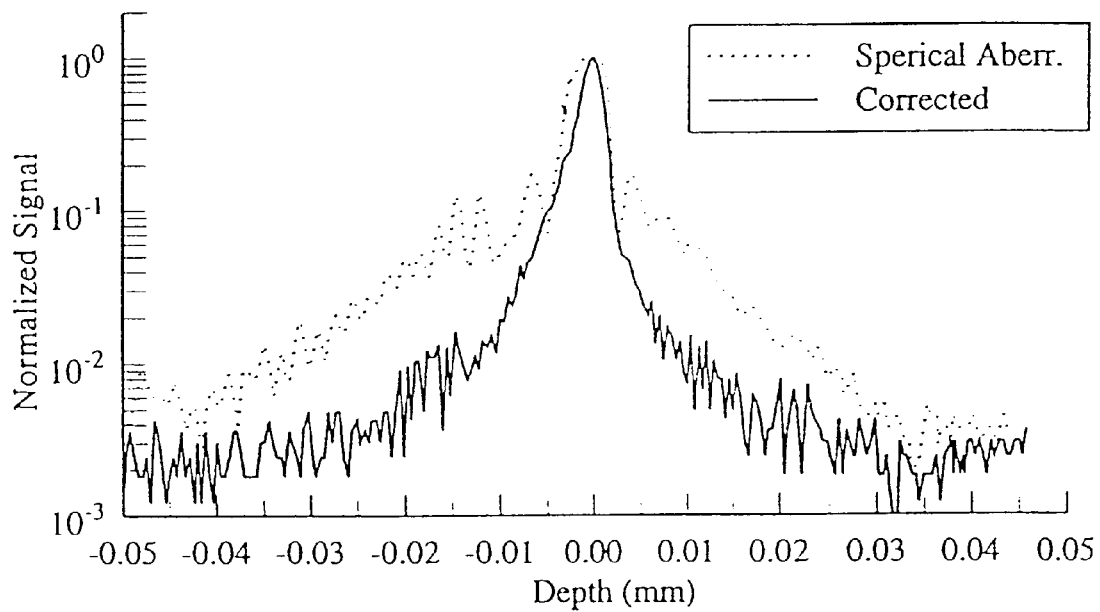
FIG. 8. shows the axial response of one embodiment of a reflectometer to a plane reflector when the conjugate image was not placed 150 mm behind the objective. The axial response of the system with the correct conjugate is included for comparison. A normalized pinhole radius of 3 was used for both scans.

In one embodiment, the conjugate image was placed 130 mm behind the objective. The effect of the aberrations on the axial response to the surface of a microscope slide is shown in FIG. 8. Most of the resolution loss was due to spherical aberration (Sheppard and Cogswell, 1991).

Unfortunately, most microscope objectives are built for transmission microscopy or epifluorescence rather than reflectance imaging and the amount of specular reflection from the lenses within the objective is not considered in its design. Although most objectives do use AR coatings, the coatings are typically designed for visible wavelengths and work poorly in the NIR. As a result, the objective may, in one embodiment, contribute the largest part of the specular reflection to the background signal.

In one embodiment, pinhole 30 may be placed in a mechanical mounting capable of translating in the three dimensions. Lens 66 may be selected so that the minimum pinhole diameter, shown as aperture 26, needed for a $v_p$ of 2, may be equal to about 10 mm. Pinholes smaller than 10 mm may need more translation sensitivity than some stages can provide.

Figure 9:
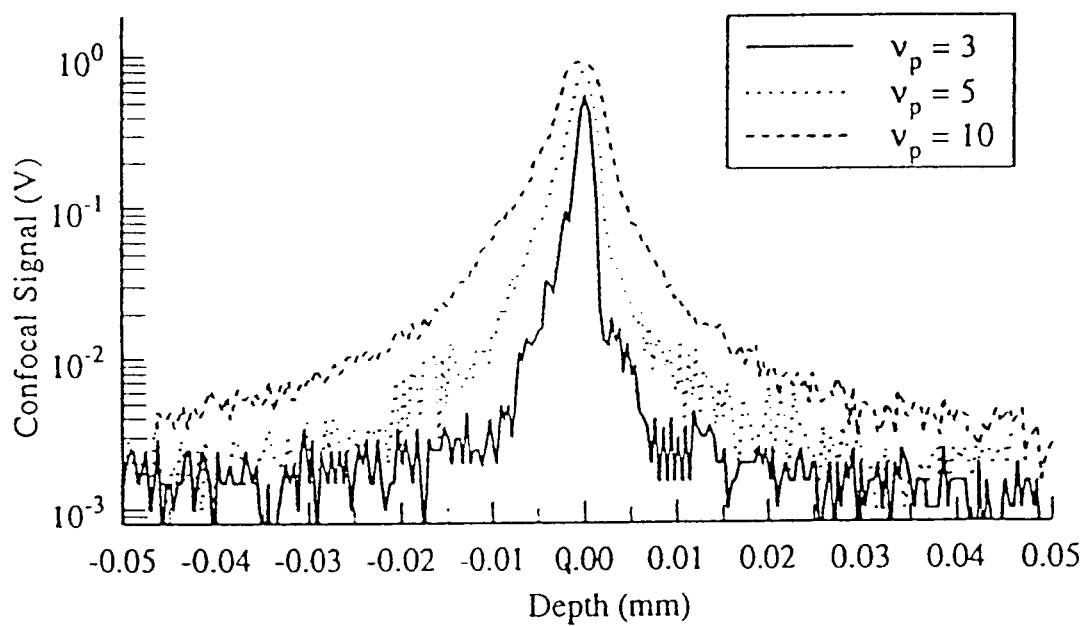
FIG. 9. shows the axial response of one embodiment of a reflectometer to a plane reflector at several pinhole diameters.
Figure 10A:
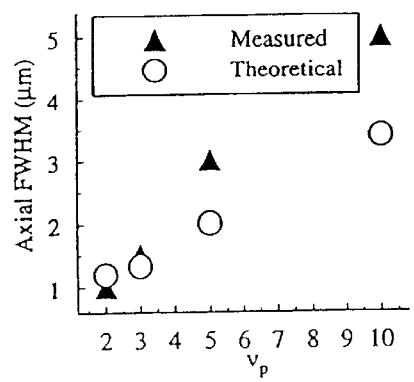
FIG. 10A. shows the measured and theoretical axial resolution FWHM for a range of normalized pinhole radii according to one embodiment.

The response of apparatus 10 to the surface of a microscope slide immersed in water may be quantified for a range of pinhole diameters. Some resulting scans are plotted in FIG. 9 for $v_p$ of 3, 5, and 10. The corresponding physical pinhole diameters were 15, 25, and 50 μm. The measured FWHM axial resolution is plotted in FIG. 10A along with the theoretical prediction for axial resolution. The measured resolution is close to theoretical expectations for small $v_p$, but less accurate at higher $v_p$. The separation between ideal and measured values matches previously published results (Wilson, 1995) in which the separation was related to the differences between the actual pupil function and the pupil function used for the theoretical calculation.

Figure 10B:
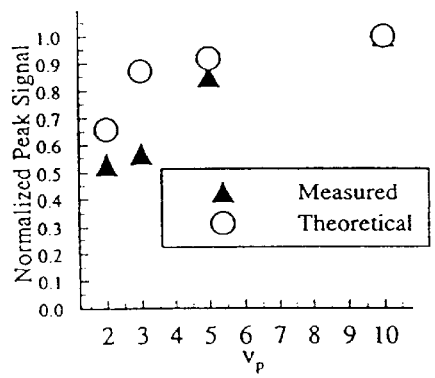
FIG. 10B. shows the signal peak amplitudes normalized to the peak amplitude for $v_p=10$ according to one embodiment. A theoretical prediction for the decay in the peak amplitudes from the value at $v_p=10$ is also plotted.

The peak amplitudes from the scans may be normalized to the $v_p=10$ peak amplitude and are shown in FIG. 10B. Theoretically, the signal amplitude has been shown (Wilson, 1995) to decrease according to $1-J_0(v_p)^2-J_1(v_p)^2$ where $J_n$ is a Bessel function of the $n^{th}$ order and first kind. In order to compare the measured to the theoretical signal amplitude, which predicts that the normalized signal will go to one as $v_p$ goes to infinity, the peak value of the largest $v_p$ used was normalized to one. The measured peak values are less than predicted for the smallest values of $v_p$. The increased loss of signal over the theoretical prediction is most likely a result of aberrations (Sheppard et al., 1994).

Figure 11:
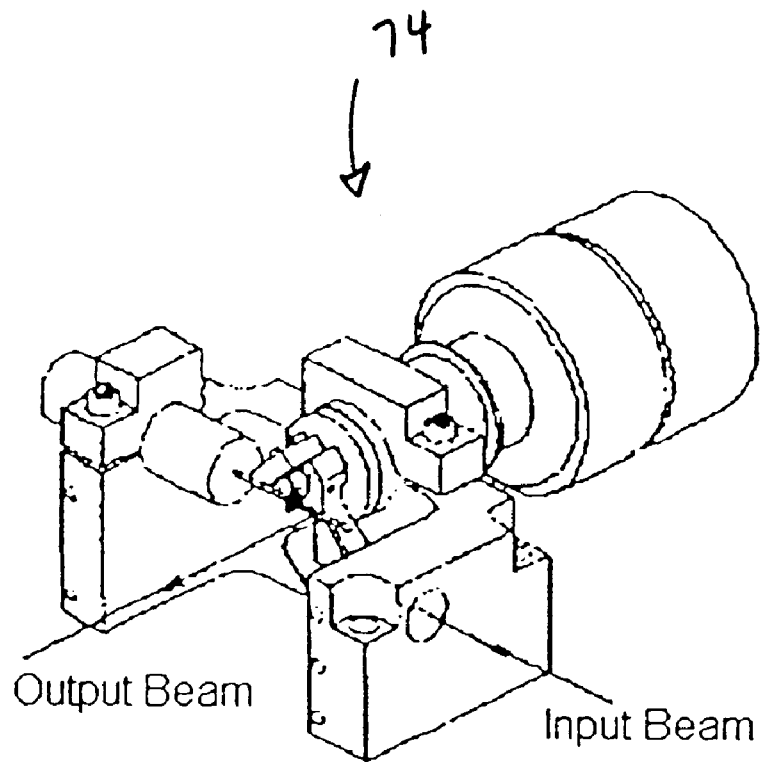
FIG. 11. is a sketch of an 8 kHz video scan head from General Scanning used in one embodiment. A galvonometer moves a paddle mirror in the page direction at 15 kHz. A smaller resonant galvo rotates in the line direction at 8 kHz.
Figure 12:
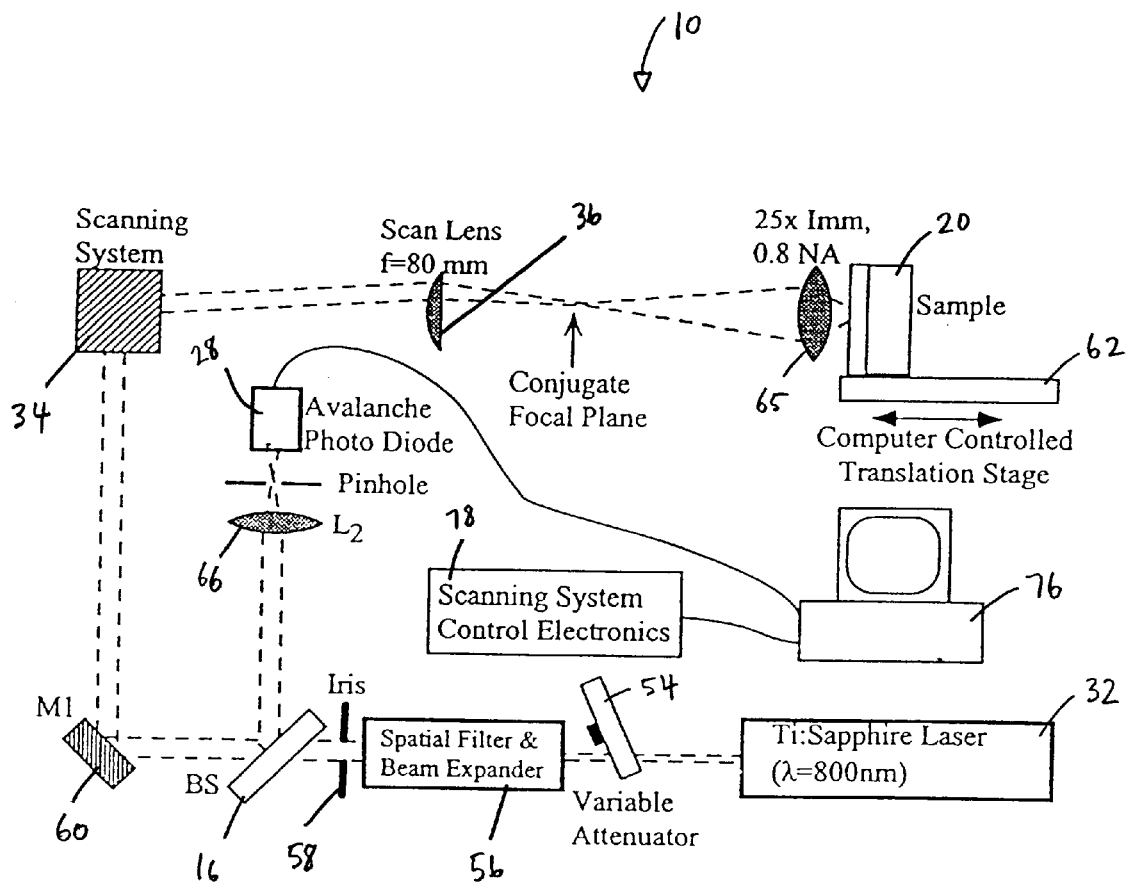
FIG. 12. is a schematic of the experimental confocal microscope.

In one embodiment, a General Scanning 8 kHz video scan head (VSH-8), pictured in FIG. 11, may be inserted in the experimental setup as part of scan system 34 as shown in FIG. 12. FIG. 12 shows an apparatus 10 including a source 32, an attenuator 54, a filter and expander 56, an iris 58, a beam splitter 16, mirrors 60, lens 66, detector 28, scan system 34, scan lens 36, objective 65, sample 20, translation stage 62, controller 76, and scanning system control electronics 78.

The VSH-8 consists of a galvanometer and a resonant galvanometer mounted at right angles in an aluminum bracket. The laser light strikes a paddle mirror mounted to a larger galvanometer in FIG. 11 and is reflected upward into the resonant galvanometer mirror. The paddle mirror scans the laser beam up and down the page at 15 Hz. The 8 kHz resonant galvanometer deflects the laser light into a line scan from its 5 mm by 7 mm diameter oval mirror. The small diameter of the mirror attached to the resonant galvanometer may be the limiting aperture of the system. The long axis of the oval mirror may be placed in the axis of the paddle mirror's rotation so that the clear aperture is 5 mm at all angles scanned.

Figure 13:
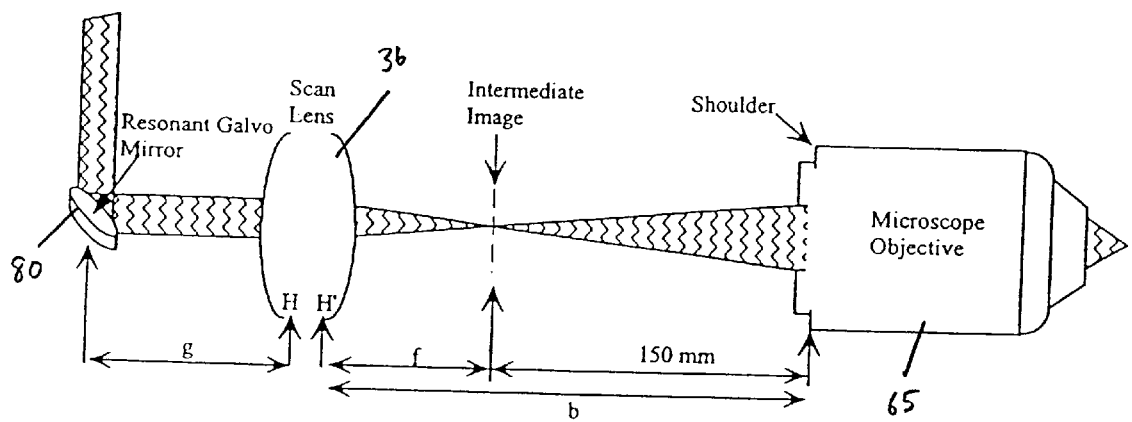
FIG. 13. is a sketch of a scan lens according to one embodiment.

Coupling lens 36 may couple the light deflected from the scan system 34 into the microscope objective 65. In one embodiment, the requirements on the design were 1) the laser light fill the back aperture of the microscope objective lens for all scan angles and 2) the light be focused at the conjugate image plane 150 mm from the shoulder of the objective 65. In one embodiment, a 25×, 0.8 NA immersion objective was selected for the system. FIG. 13 shows the design requirements and variables according to one embodiment.

In one embodiment, to construct images from the detected secondary radiation, it may be necessary to sample the voltage of the APD detector 28 in a sequential pattern to form the pixels within each line and the lines of a video frame. The VSH-8 control electronics may provide timing signals to a video acquisition computer card, which may be a part of control electronics 78, as to when each pixel was sampled, when a line started and stopped, and when a frame (image) started and stopped.

Figure 14:
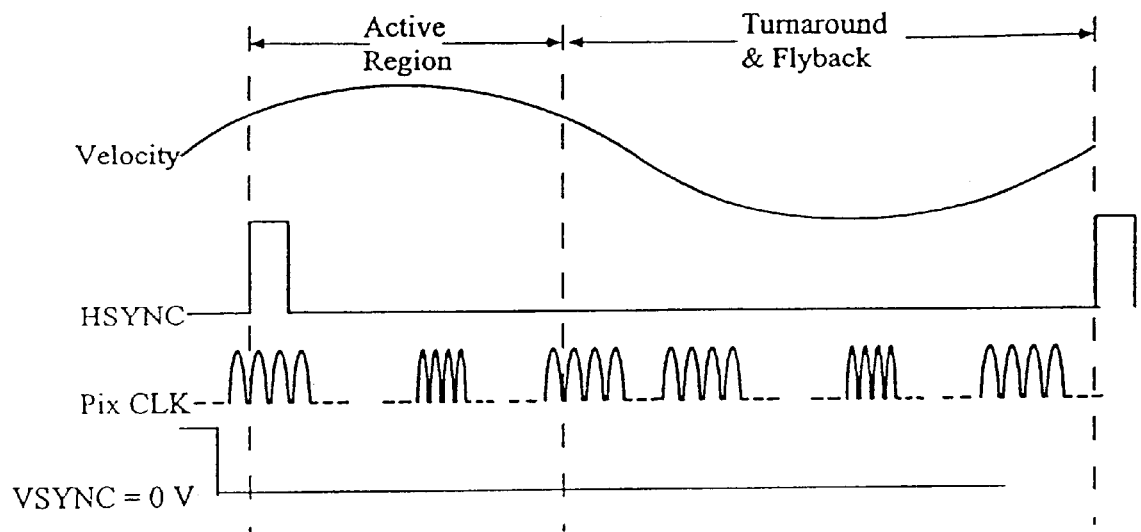
FIG. 14. is a timing diagram of signals from a scan system control electronics for one cycle of a resonant scanner according to one embodiment.

The general shape and timing of these signals is shown in FIG. 14. A frame acquisition may begin with the vertical sync clock (VSYNC) dropping from 5 V to 0 V. At the next rising edge of the horizontal sync clock (HSYNC) the video card may begin to sample pixels from the APD voltage at intervals given by the rising edge of the pixel clock (Pix CLK). The video card may be programmed to sample 512 pixels for each line. In one embodiment, no pixels were acquired during the time required for the mirror to reverse direction and fly back to the beginning of the next line. The next line began with the next rising edge of the HSYNC signal. A frame was completed after acquiring 512 sequential lines. The next frame started on the falling edge of the VSYNC signal.

Because the velocity of the resonant galvanometer may be sinusoidal, the frequency of the pixel clock varied sinusoidally as well. In one embodiment, at the start of a line's active region the frequency was approximately 7.5 MHz. It rose to 15 MHz in the middle of the line and returned to 7.5 MHz at the end of the line. The varying frequency of the pixel clock presented a problem for commercially available video cards. Most video cards are manufactured to acquire the RS-1170 standard composite video signal which uses a pixel clock of a fixed frequency. In fact, all known video cards employ a phase-lock-loop (PLL) to lock onto the pixel clock frequency. A card with a PLL is unable to skew its center frequency from 7.5 to 15 MHz and back again to 7.5 MHz within each line. In addition, many video cards expect the signal voltage to drop to a reference level, or black level, before the start of each line to which a gain of an amplifier is set. No reference level existed in the APD voltage used here. Video cards from Dipix (Dipix Technologies Inc., Ottawa, Ontario, Canada), Matrox (Matrox Video Products Group, Quebec, Canada), Epix (Portland, Oreg.), Data Translation (Data Translation, Inc., Marlboro, Mass.), and MuTech (MuTech Corporation, Billerica, Mass.) were evaluated for their ability to handle both of the above problems. Only the MV-1000 video card from MuTech appeared to capable of bypassing its PLL. A MV-1000 card was acquired and placed in the PCI local bus of a Pentium 200 MHz computer. The high bandwidth of the PCI bus was needed to display the acquired images on the computer screen at 15 frames a second. However, it was discovered that the MuTech card was not able to bypass its PLL and could not acquire images using the pixel clock from the scanning system. A working solution was to program a constant sampling frequency of 11 MHz into the video card. Using a frequency halfway between the needed values aligned the pixels in adjacent lines enough to form a cohesive image of the test target. Because the frame grabber was acquiring at a fixed frequency while the pixel clock frequency continued to vary, the acquired images were sinusoidally distorted. The video card was also programmed to low pass filter the sampled data at 5 MHz to avoid violating the Nyquist sampling criteria. To date, MuTech has been unwilling or unable to rectify the problem with the PLL and pixel clock. The only possible solution may be physically altering the video card to bypass the PLL.

In one embodiment, software was written to control the video card and display the acquired images on the computer screen (Prasankumar and Gopinath, 1997). The program was constructed from the MCC foundation class libraries in the C++ language. A windows-based 32 bit program was compiled under the Windows NT operating system.

The card converted the analog voltage into 256 digital gray levels. Several acquisition control options were given to the user through drop down menus. The analog voltage range over which the 256 levels are digitized was selected by the user with a maximum range of 0 to 5 V. The 256 levels were digitized on a linear, log, or inverse linear scale through the use of a look up table (LUT). Using logarithmic digitization increased the visibility of the small amplitude signals; however it also increased the visibility of the shot noise in the image. As such, more contrast was observed in the image using the linear or inverse linear scale. Whether to use the linear or inverse linear scale was a user preference although the following results demonstrate that each method appeared to bring out different features in the same image. The user also had the option to scale the input voltage signal by a DC offset of −2.5 to 2.5 V before digitization. Typically an offset was used to compensate for a background signal or to boost the voltage of the signal into the digitization range. Ideally the acquired images used the entire range of 256 levels (Castleman, 1979). To assess the number of gray levels being used, the program displayed a histogram next to the image. The histogram was updated 15 times per second. The gray levels of the image were equalized by adjusting by the laser power, A/D range, and/or the DC offset.

In one embodiment, images of interest may be frozen, or grabbed, by the software and saved to a file. To record dynamic events, the real time video was captured on a super VHS video tape. An adapter (ADS, SuperScan 2, ADS Technologies, Cerritos, Calif.) was placed in the cable between the computer and monitor to convert the monitor's SVGA signal to the super VHS format which was fed into the SVHS VCR. Individual video frames of interest on the tapes were played back on an editing VCR and captured to a computer file by a video frame grabber.

In one embodiment, a contrast agent may be used to aid in imaging. In one embodiment, breast cancer cells were imaged before and after exposure to acetic acid. The image of the native cells may resolve the nuclei and the cell membrane, however the contrast may vary from cell to cell. In one embodiment, the addition of 20 $\mu$l of 6% acetic acid to 200 $\mu$l of the native cells in saline may cause a dramatic increase in the signal from the nuclei and the intra-cellular contents. The same illumination power may be used for all images. The cell nuclei and cell outline may become very distinct with the addition of acetic acid and the contrast may be increased from the image of native cells. ALA may also be used as a contrast agent. Again, the signal from the cell may increase, however, only the contrast to the outline of the cell. In other embodiments, toluidine blue, hypertonic saline, hypotonic saline, or iodine may be used as contrast agents In one embodiment, specular reflections may be reduced from fiber bundle 38. One obvious reduction method is to place anti-reflection coatings on the faces of bundle 38. The highest efficiency AR coating could have reduced the reflections from 4% to 0.3% of the incident power. Commercial confocal microscopes have utilized polarization based techniques to reduce the reflections by approximately three orders of magnitude. However, the fiber optic bundle 38 may not maintain the polarization of the light traversing it, thereby reducing the effectiveness of polarization control.

In one embodiment, an oil—index matched to the index of the fiber bundle 38 in the space between the scan lens 36 and the bundle 38 may be used. Ideally an oil with an index of refraction matching that of the fiber bundle 38 could be used to eliminate the reflection from the bundle faces. However, there are at least two indices of glass in a typical bundle; one glass for the fiber cores and another for the claddings. The difference in the index of the two glasses can be quite large. There are three manufacturers of fiber optic bundles: Schott, Sumitomo, and Fujikura. The Schott fiber bundle uses a core index of 1.58, a cladding index of 1.48, and a filler glass with an index of 1.61 in the spaces between the claddings. The other two manufacturers use fused silica for the cladding and a Germanium-doped fused silica core. The Sumitomo bundle uses a core index of 1.494 and a cladding index of 1.453. Fujikura states that the absolute index of the core and cladding is proprietary information so the values for the indices were extrapolated from the material description and the given 0.41 NA. The calculated core index was 1.51 assuming the fused silica cladding has an index of 1.45.

In one embodiment, if an oil with an index equal to the fiber core is used, large reflections from the cladding may be seen from the proximal end 40 of the fiber. In one embodiment, an immersion oil index was used that was about halfway between the core and cladding indices at the proximal end 40. Although a reflection may still be seen from the core and cladding, its amplitude may be constant over the face of the bundle. The detected D.C. signal from the APD may then be high pass filtered to remove the specular portion. At the distal end 42, an immersion oil with an index equal to the core index of the fiber bundle 38 may be used to essentially eliminate the specular reflection from that face.

In one embodiment, one of the assumptions for the required reduction in specular reflection was a laser coherence length less than the separation between the fiber faces and the image plane. Theoretically, the reflection from the distal end of the fiber could be eliminated by matching the index of the immersion oil exactly to the core index. In reality, it may not be possible to totally eliminate the reflection. As such, the coherence of the laser may be required to be less than the 10 cm separation between the distal end of the bundle and the image plane. In one embodiment, a diode pumped Nd:YAG laser manufactured by Uniphase was used as source 32.

Figure 15:
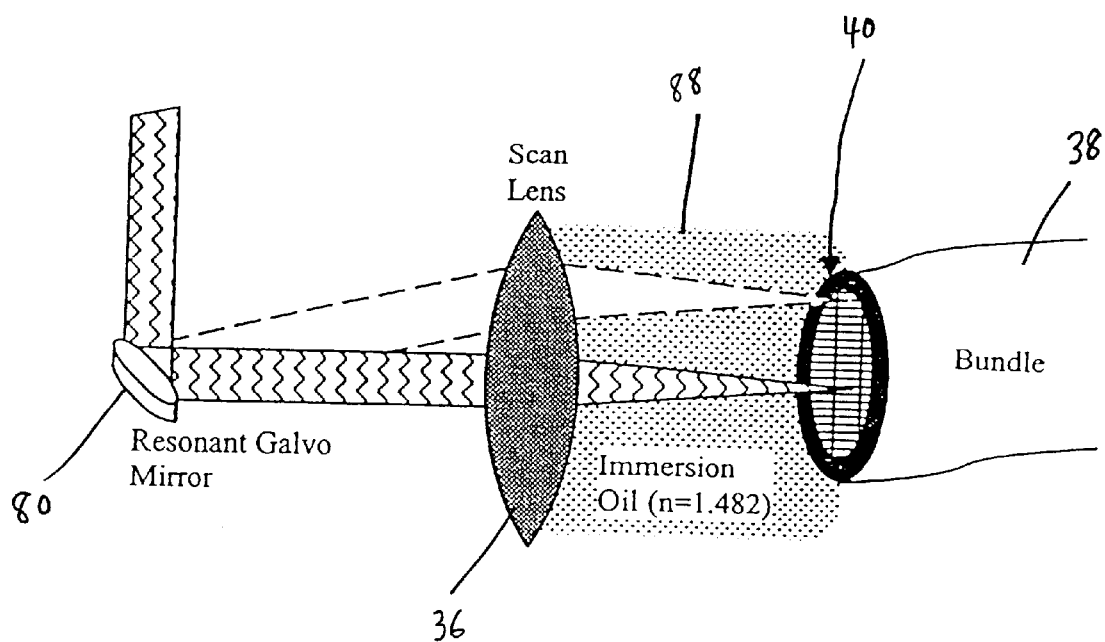
FIG. 15. is an illustration depicting a telecentric scan lens according to one embodiment.
Figure 16:
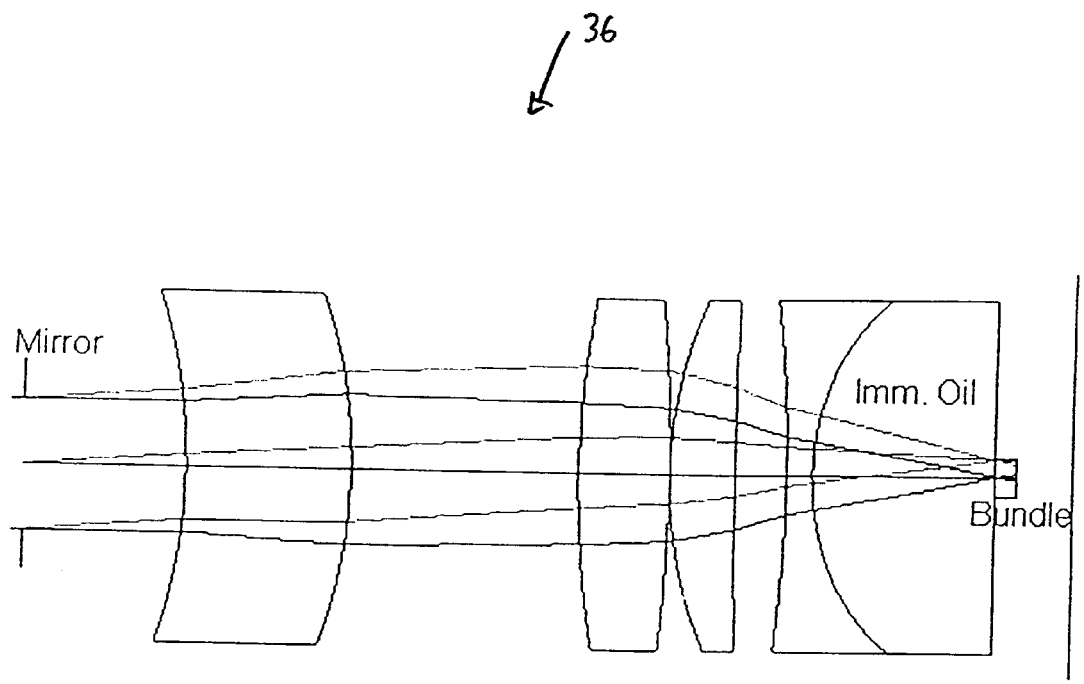
FIG. 16. shows an optical layout of one embodiment of a scan lens.
Figure 18:
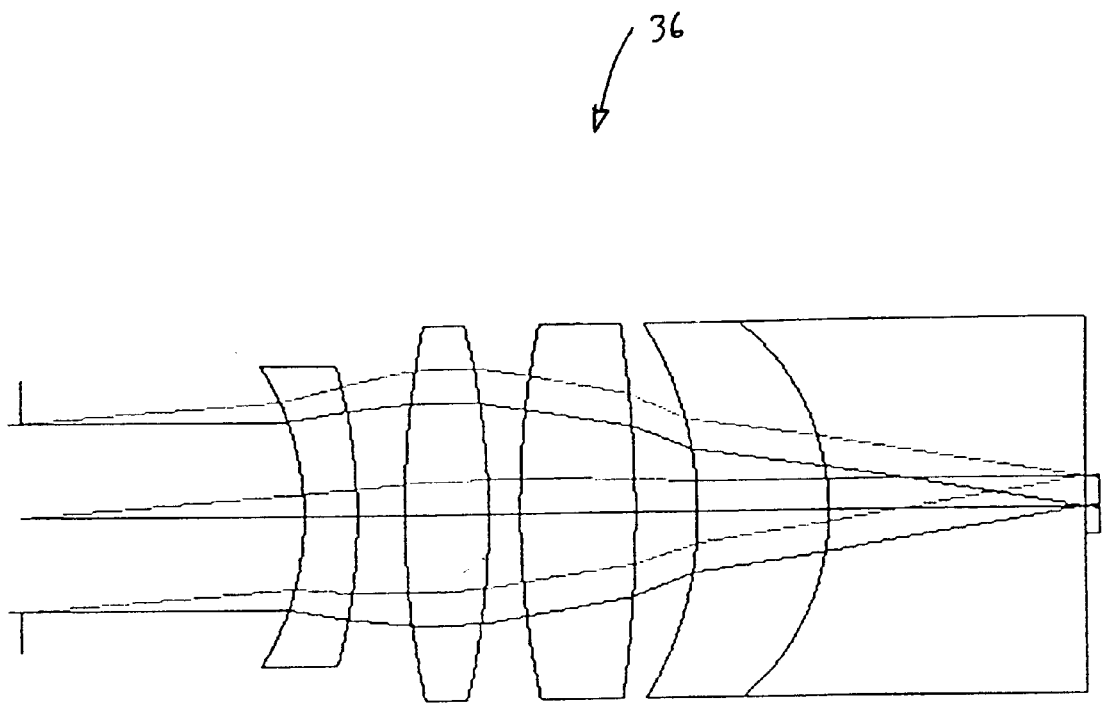
FIG. 18. shows an optical layout of one embodiment of a scan lens.
Figure 20:
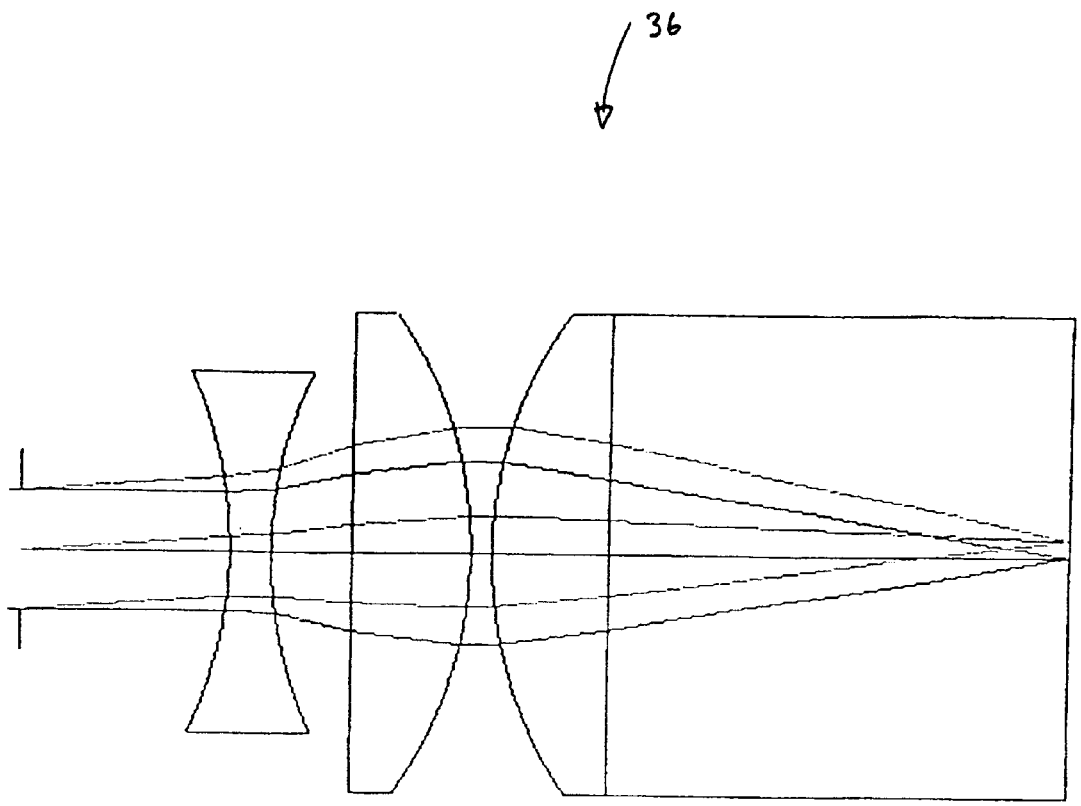
FIG. 20. shows an optical layout of one embodiment of a scan lens built with stock catalog elements.

FIG. 15 shows one embodiment of scan lens 36. Also shown are galvanometer mirror 80, proximatal index matching agent 88, and fiber bundle 38. The NA of the scan lens may be determined by two factors: the required magnification of the endpiece and the diffraction limit to the spot size. In one embodiment, scan lens 36 may have a NA of about 0.2, but it will be understood that other NA may be used according to, for instance, specific design specifications. FIGS. 16, 18, and 20 illustrate alternative designs according to other embodiments.

Figure 17:
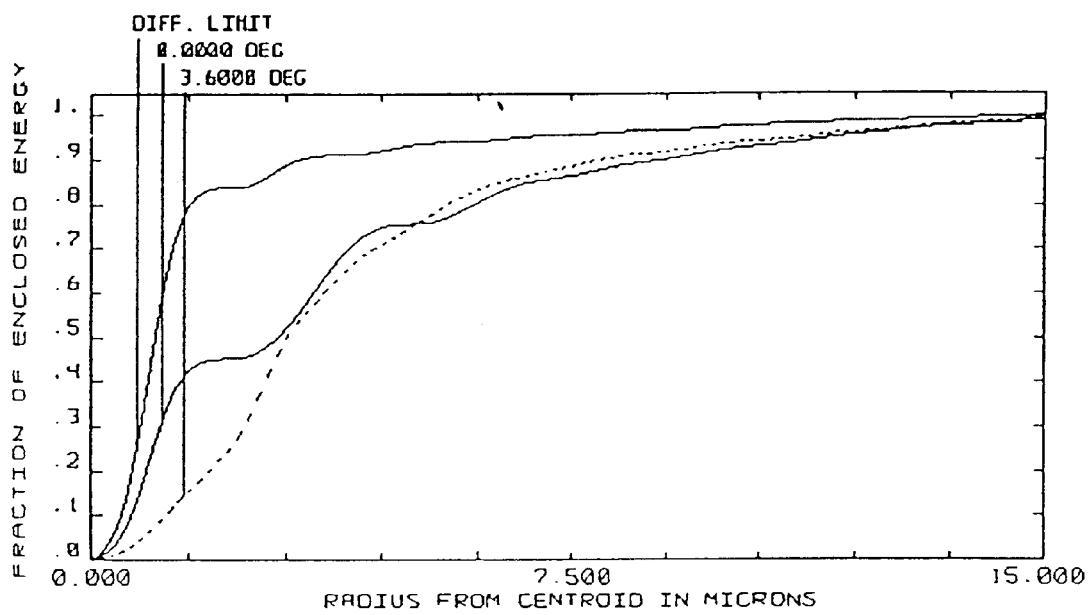
FIG. 17. is a plot of the encircled energy vs. radius from the centroid of the focus for one embodiment. Plots are shown for the resonant mirror normal to the axis and at the maximum required scan angle.

FIG. 16 shows a lens as modeled by Zemax. A plot of the encircled energy for this design is shown in FIG. 17 to demonstrate that the lens had significant aberrations when used in the scan lens application. Plots are shown for the resonant mirror normal to the optical axis and at the maximum required scan angle of 3.6 degrees. The major cause of the aberrations was the addition of the index matching oil in the image space. The dominant aberrations in the Seidel aberration coefficients were spherical and coma.

Figure 19:
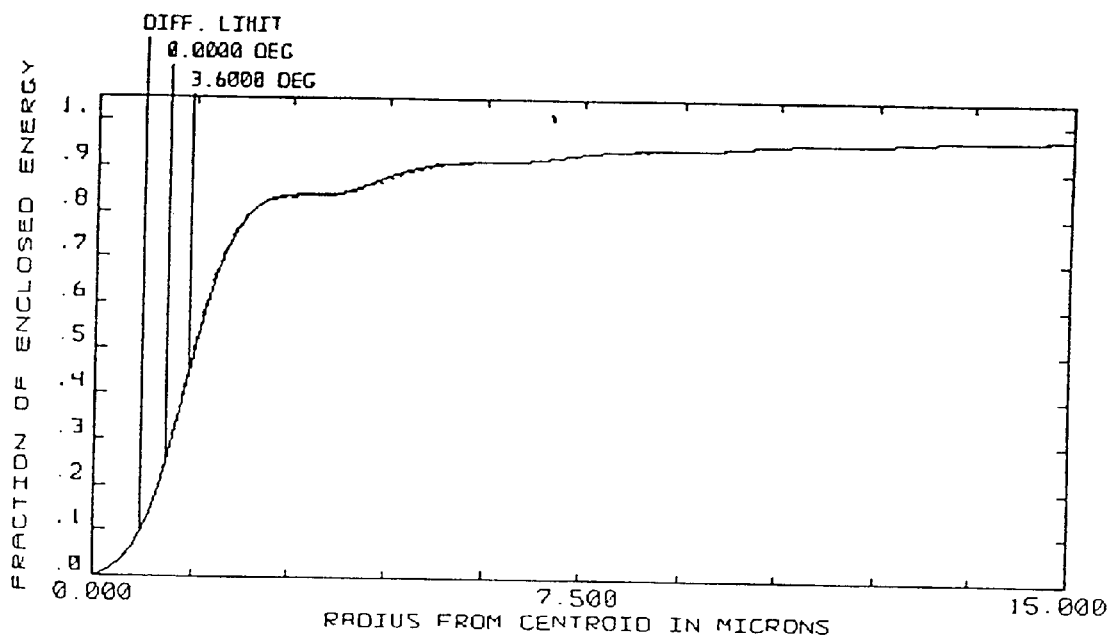
FIG. 19. shows an encircled energy plot for a design according to one embodiment. The plots for the on-as focus (0 deg) and the marginal focus (3.6 deg) are overlapping the diffraction limit plot.

To correct the aberrations, the the thickness, spacing, and curvature of the elements may be minimized. Another embodiment of scan lens 36 is shown in FIG. 18. The encircled energy plot is shown in FIG. 19.

Figure 21:
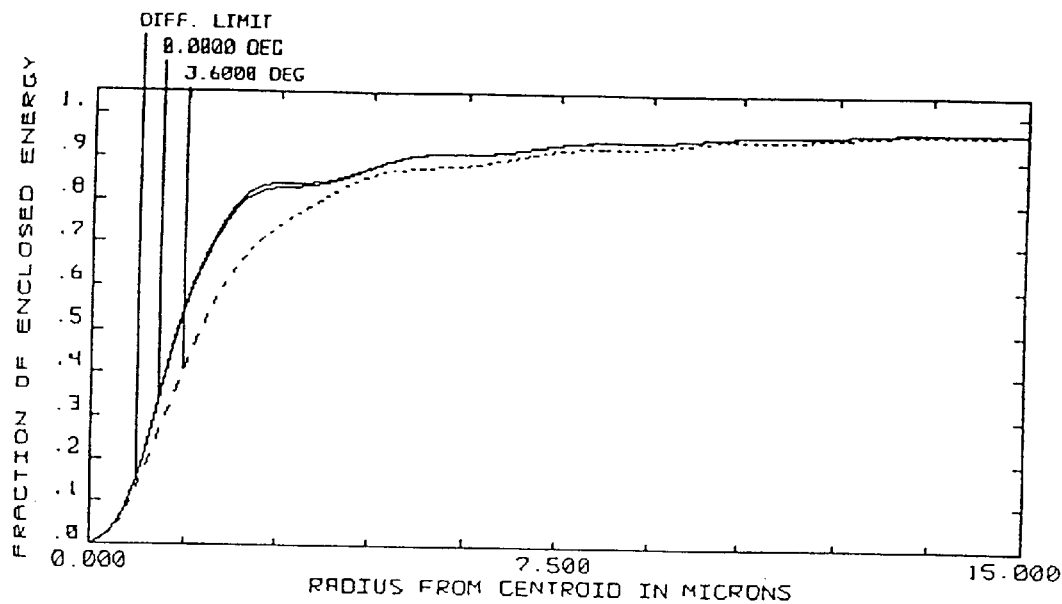
FIG. 21. is an encircled energy plot of a stock scan lens according to one embodiment.

FIG. 20 shows another scan lens 36 design. The design was obtained with a pair of Sapphire plano-convex lenses (Melles Griot, 01LSX009/126, Irvine, Calif.). The encircled energy plot of the lens is shown in FIG. 21. The on axis focus was diffraction limited, however, the marginal focus was less than diffraction limited. Spherical aberration from the first sapphire lens was the principal cause. The gaussian beam analysis predicted a 3.4 $\mu$m waist diameter on axis.

In one embodiment, design objectives for the coupling lens included the control of the magnification in the endpiece to fill the back aperture of the microscope objective 65 and to immerse the distal end 42 of the fiber bundle 38 in a distal index matching agent. In one embodiment, a de-magnification of 0.25 between the fiber bundle 38 and the image plane was used to achieve a desired resolution. A 40×0.75 NA water immersion objective was chosen for the microscope objective.

Figure 22:
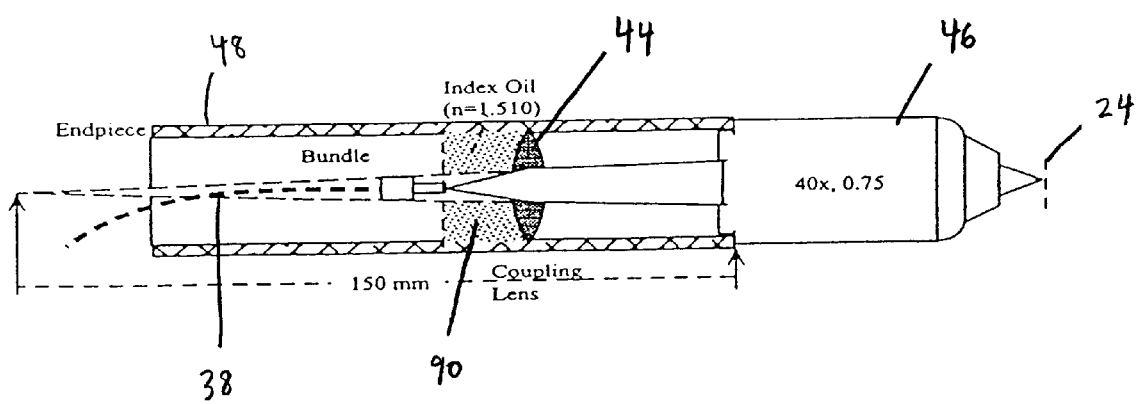
FIG. 22. is an illustration of one embodiment of an optical arrangement in the endpiece. The NA of the light from the fiber bundle is modified by the coupling lens so that the objective sees the light as coming from a virtual focus 150 mm away.
Figure 28:
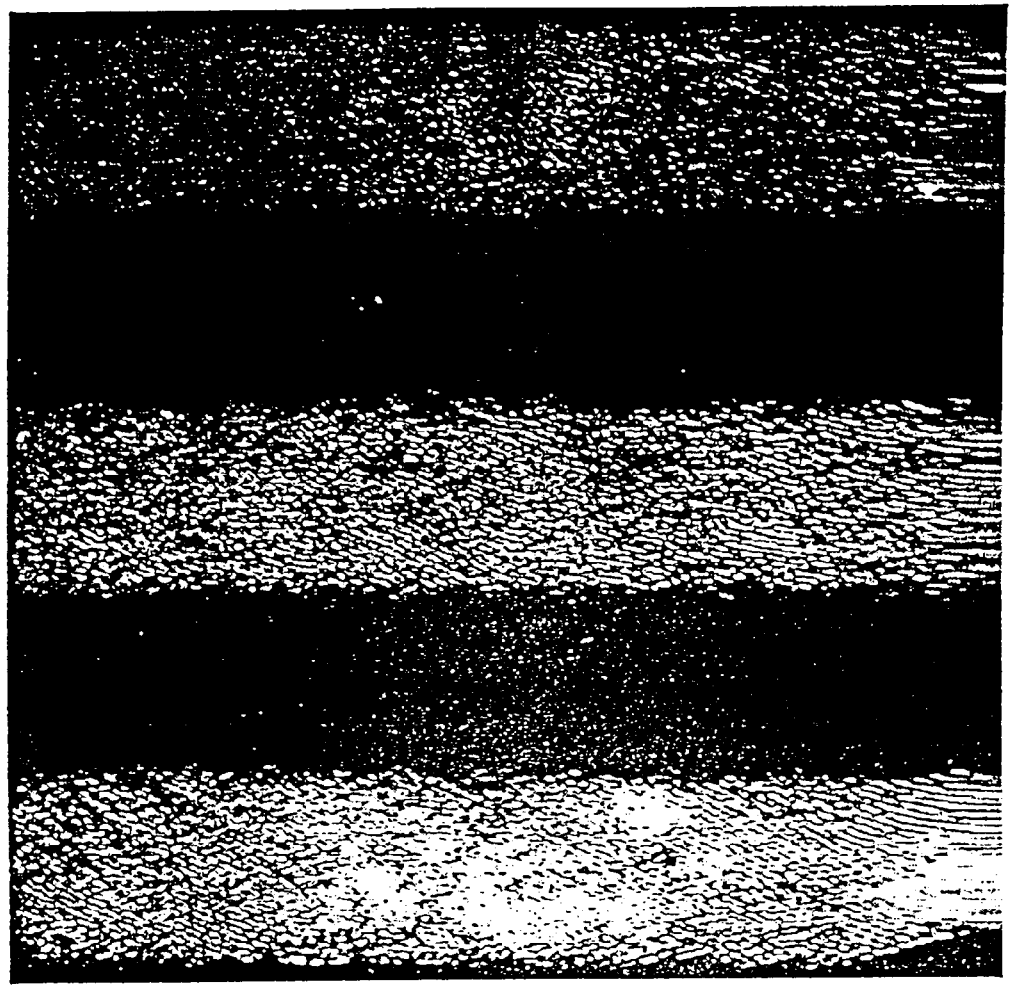
FIG. 28. is a confocal image of a mirrored grating taken with one embodiment of a fiber optic system. Spacing between lines is 25 $\mu$m.

FIG. 22 depicts the arrangement between the lenses in the endpiece. FIG. 22 shows bundle 38, endpiece 48, distal index matching agent 90, coupling lens 44, objective 46, and image plane 24. The aberrations of the objective 46 may be corrected if the light enters the objective from a virtual focal plane about 150 mm behind the objective 46 shoulder. This is shown in FIG. 28 by the dashed lines. To fill the 7.5 mm objective aperture, the light would be leaving the 150 mm conjugate focus with a 0.02 NA.

In one embodiment, the function of the coupling lens was to modify the NA of the light exiting the fiber bundle from a 0.2 NA to a 0.02 NA. In addition, in one embodiment, the coupling lens may fill the 7.5 mm back aperture of the objective. In an embodiment using oil as distal index matching agent, the index of the oil in front of the bundle 38 may be selected to match the index of the fiber cores.

Figure 23:
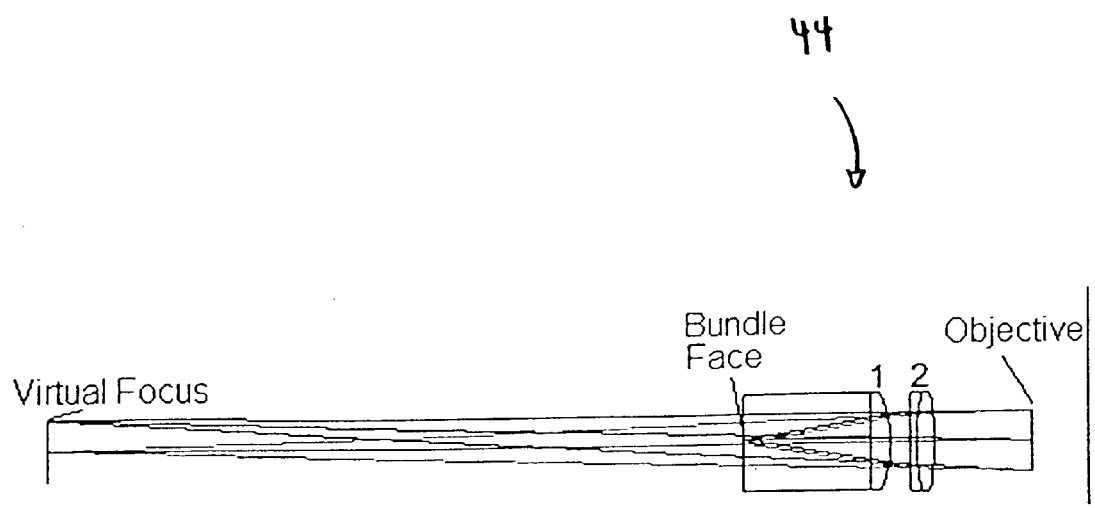
FIG. 23. is an optical layout of one embodiment using a commercial doublet lens and an optimized singlet. The space between the fiber bundle face and first element is filled with index oil.

One embodiment of a coupling lens system 44 is shown in FIG. 23 in which the light emerges from a fiber on-axis and at the margin of the bundle. With this design less than 0.2 waves of optical path difference was estimated at the virtual focus and the light from both fibers was centered on the objective aperture with the correct diameter.

In one embodiment, a system of mechanical mountings to align and hold the elements at the specified distances was designed (Bowman, 1997). A diagram of one setup for scan lens mounting is shown in FIG. 24.

Figure 24:
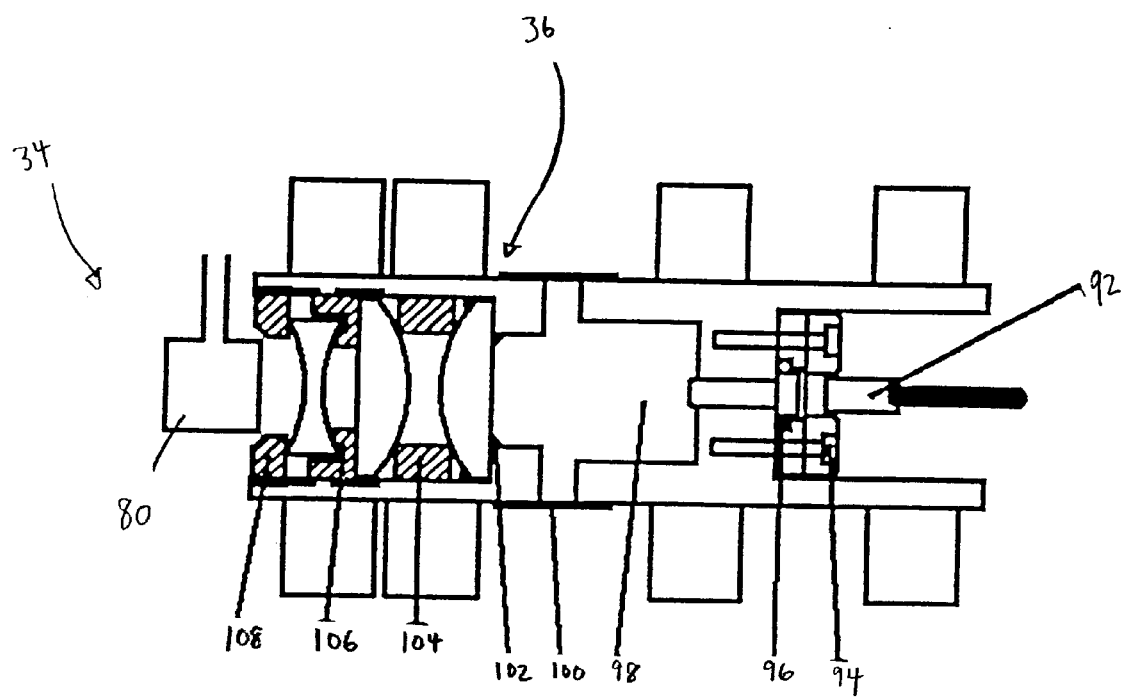
FIG. 24. is a diagram of one embodiment of a mechanical mounting system for a scan lens.

In the embodiment of FIG. 24, fiber bundle 38 may be epoxied within an SMA connector 92 and attached to the housing by a plate and three screws 94. The connector 92 may be inserted into a reservoir 98 with an O-ring 96 seal. The mounting of the scan lens 36 and the fiber bundle 38 may be separated by a rubber membrane 100 to allow for axial translation of the bundle 38 through the focus of the scan lens 36. The opposite end of the chamber may be sealed by epoxy glue 102 placed around the plano face of the lens. The separation between the lenses may be controlled by the thickness of the spacers 104 and 106 and the locking ring 108.

Figure 25:
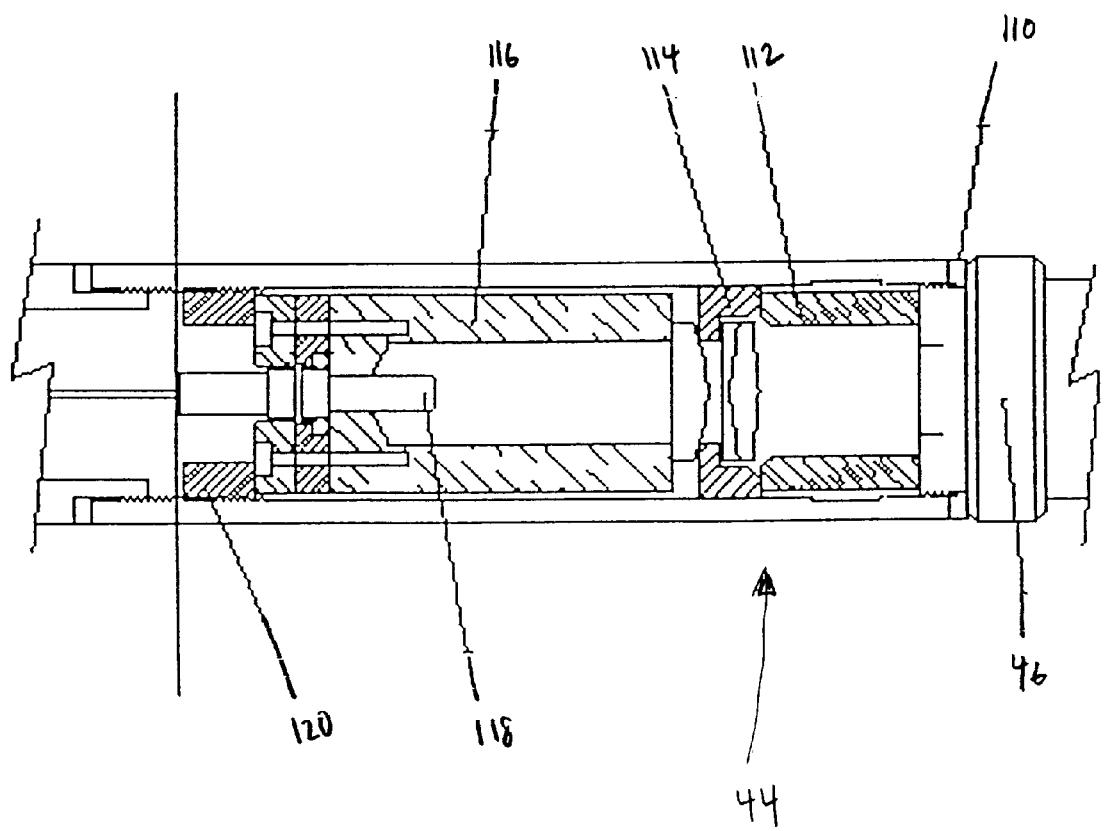
FIG. 25. is a diagram of one embodiment of a mechanical mounting for a coupling lens.

One embodiment of a coupling lens mounting is shown in FIG. 25. A 40× microscope objective 46 may be threaded onto the endpiece. An O-ring 110 may be placed between them for a water tight seal. The separation between the lenses may be controlled by the thickness of the spacer 112 and lens mount 114. Silicone RTV glue may be used to seal the reservoir 116 with the plano side of the singlet lens. The fiber abundle 38 may be epoxied into an SMA connector 118 which may be immersed in index matching oil. The assembly may be held within the endpiece by the locking collar 120.

Figure 26:
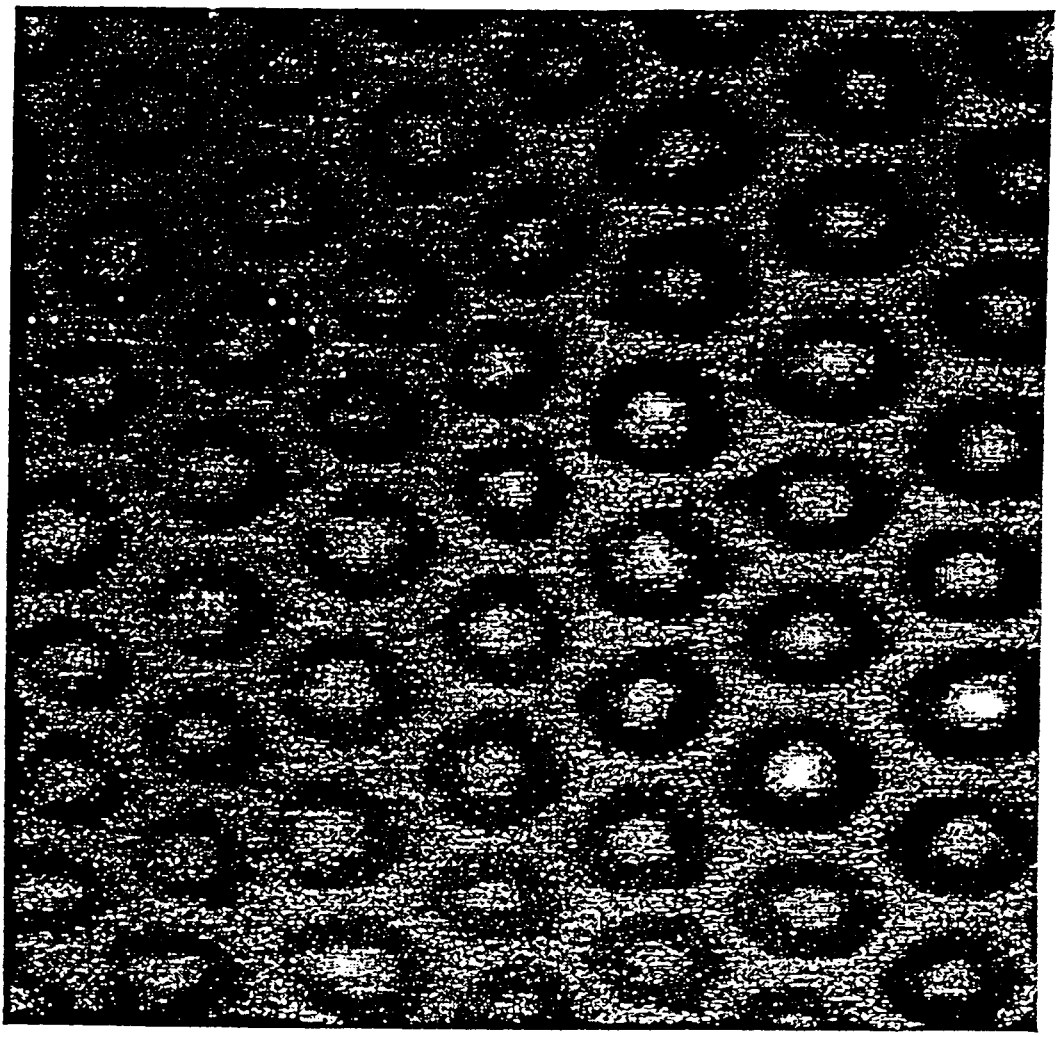
FIG. 26. is an image of a Fujikura fiber bundle face immersed in an oil with a 1.463 refractive index. The distal end of the bundle was immersed in a 1.505 index oil.

To assess the efficiency of rejecting the specular reflections with refractive index matching, the proximal face 40 of the immersed fiber bundle was imaged with the confocal microscope. Initially, oils with indices of 1.478 and 1.506 (Cargille Labs, Cedar Grove, N.J.) were used at the proximal and distal end, respectively. The indices of the oils were scaled from the design values to account for the change in wavelength to 1064 nm. The image from this arrangement showed a larger signal from the cladding rather than the anticipated equal intensity. The index of the oil at the proximal end was reduced until the signal from the core and cladding become approximately equal. FIG. 26 shows an image of the bundle face with an index of 1.463 at the proximal end and 1.505 at the distal end. The image shows that the reflections from the fiber cores were not uniform across the core diameter. An index of 1.463 was chosen as the optimal value to use at the proximal end of the bundle since it made the reflection from the cores slightly greater than the cladding. On average, a ratio of 1.3 was seen between the signal intensity in the center of the cores and the cladding. Varying the index of the oil at the distal end from 1.505 did not change the core reflection intensity indicating that the amplitude of the reflection from the distal face is insignificant compared to reflection from the proximal end. An index of 1.505 was chosen for the endpiece. With the selected oil indices in place, the detected specular reflection from the front face was approximately $5 \times 10^{-6}$ of the laser power into the system. Methods for dealing with the varying specular reflection are presented in the following discussion.

Figure 27:
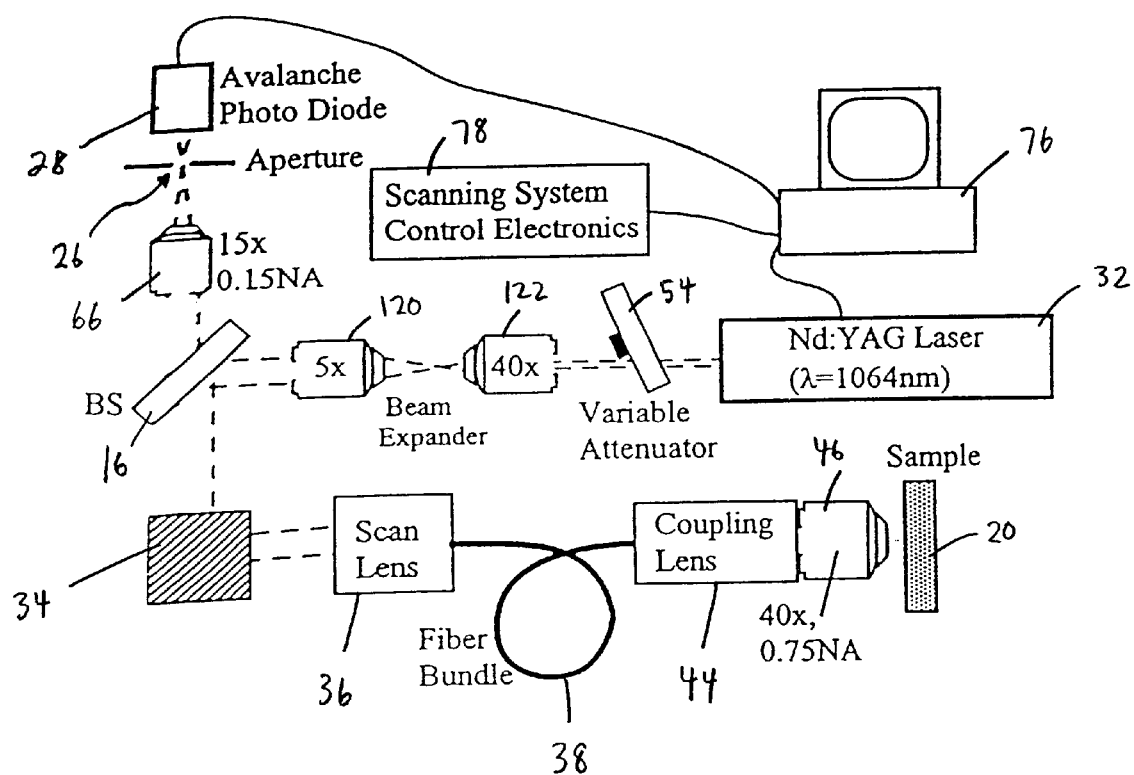
FIG. 27. is a diagram of an assembled fiber optic confocal microscope according to one embodiment.

A diagram of one embodiment of an assembled fiber optic confocal microscope is shown in FIG. 27. FIG. 27 shows a source 32, a variable attenuator 54, objectives 120 and 122, beam splitter 16, objective 66, aperture 26, detector 28, scan system 34, scan lens 36, fiber bundle 38, coupling lens 44, objective 46, sample 20, controller 76, and electronics 78.

In this embodiment, the 1 mm beam from the Nd:YAG laser was expanded to 6 mm by the pair of microscope objectives. A beam splitter 16 with a reflection coefficient of 27% was used to increase the fraction of signal passing to the detector 28. As a result, the illumination power and the corresponding specular reflection was reduced. The scan lens 36 was aligned to the optical axis by centering the reflections from the lens surfaces back onto the illumination path. To align the axis of the fiber bundle 38 with system, the light from a lamp illuminating the distal end 42 of the bundle 38 was imaged back through the system. The position of the lens assembly was adjusted to center the light from the bundle 38 on the aperture of the 5× objective 120. A 50 $\mu$m diameter aperture 26 was placed in front of the APD detector 28 to reject the light returning from adjacent fibers.

An image of a mirrored grating acquired by the fiber microscope of FIG. 27 is shown in FIG. 28. The distance between the lines is 25 $\mu$m lines. No instability due to interference was observed. The measured lateral resolution from the image was 5 $\mu$m±2 $\mu$m standard deviation. The measured FWHM axial resolution from scanning a mirror through the focus was 15 $\mu$m. The anticipated spatial resolution from the design analysis was 2.5 $\mu$m in the lateral direction and 2.8 $\mu$m in the axial direction. The observed field of view was 170 $\mu$m rather than the anticipated 210 $\mu$m. Because a scan angle of ±2.2 degrees spanned the diameter of the bundle 38 as expected, the difference in field of view must originate in the coupling lens. When the fill scan angle was used, bright reflections from the aluminum SMA connector were seen in the corners of the image. The scan angle was reduced to ±1.5 degrees to avoid the signal blooming caused by the bright reflections.

Figure 29:
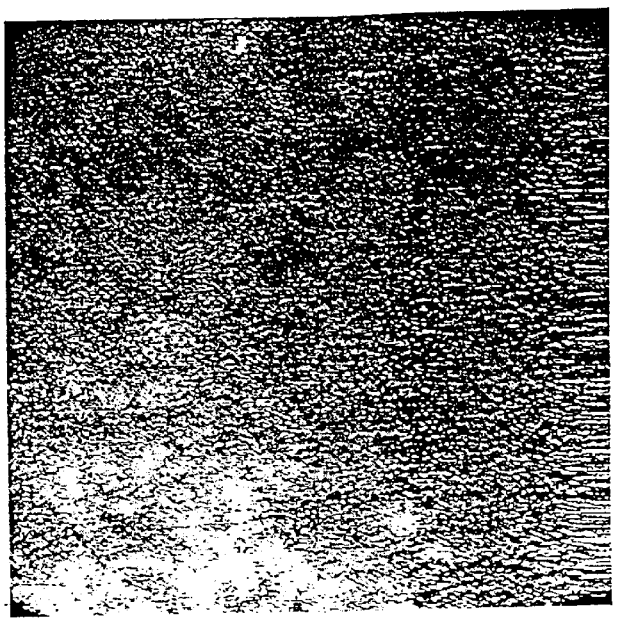
FIG. 29. is a confocal image of a mirror with a 99% reflectance at 1064 nm taken with one embodiment of a fiber optic system.

An image of a planar mirror analyzed by the apparatus in FIG. 27 is shown in FIG. 29. The image shows a mottled pattern in the detected signal. This same mottled pattern was observed in an image of the fiber bundle face acquired during the evaluation of the scan lens. In that particular image, the major source of signal was the glass/air reflection at the distal end of the bundle. Although unclear, the pattern may indicate a varying coupling efficiency of the laser light into the uneven spatial distribution of the individual fibers. FIG. 29 also shows a drop in the intensity of the signal between the bottom and top of the image. Possible causes for the drop off include vignetting of the light in the endpiece or an increase in the scan lens focal spot diameter at the top of the image.

Figure 30:
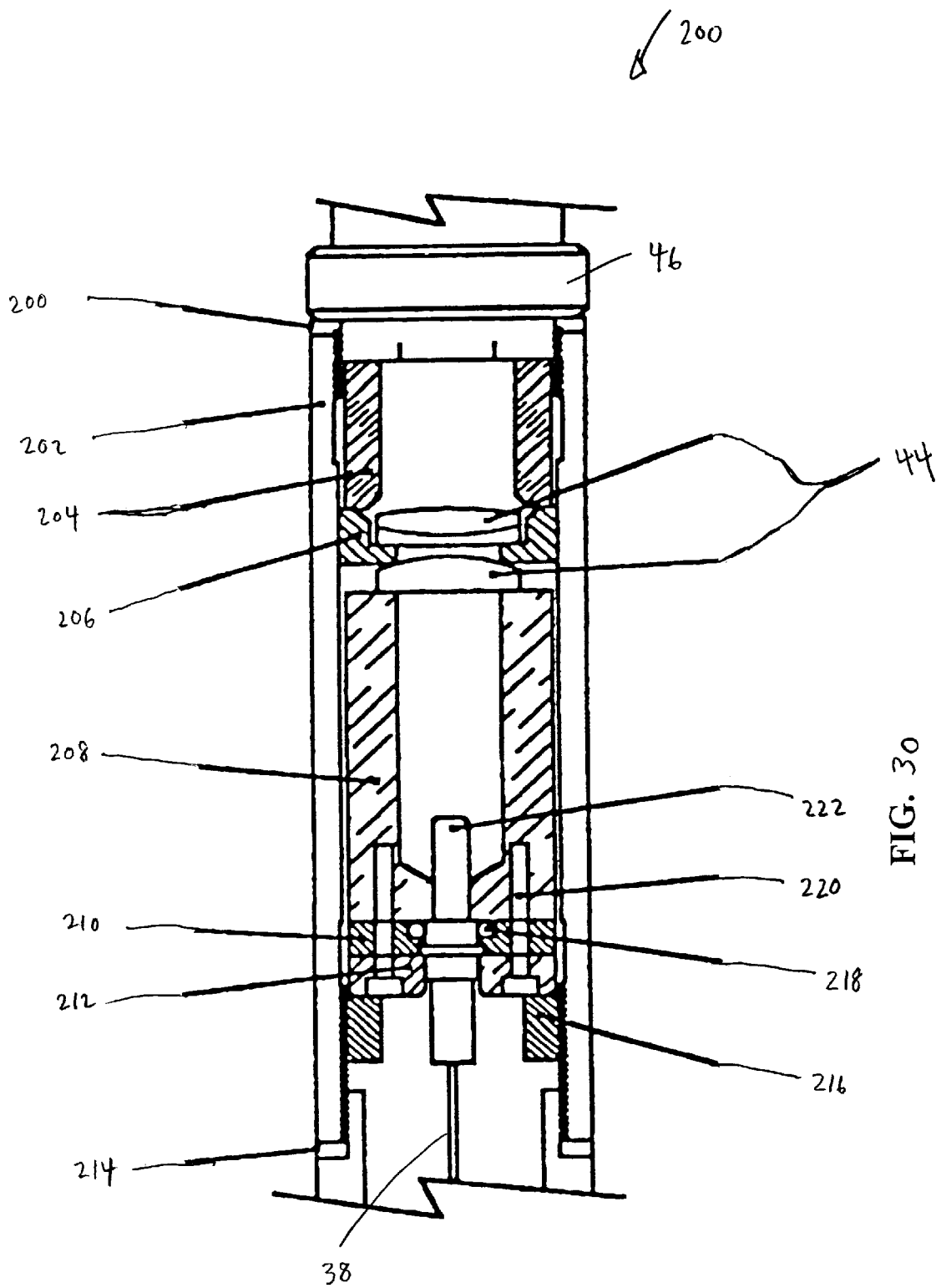
FIG. 30 shows an endoscope assembly according to one embodiment.

In one embodiment, an endoscopic confocal imaging apparatus is provided. An endoscope may be constructed in accordance with the disclosure herein, and may include elements shown in, for example, FIG. 2. However, to form an endoscopic apparatus, and endoscope portion must be formed. FIG. 30 shows an endoscope according to one embodiment of the presently disclosed methods and apparatus. In this embodiment, the endoscope 200 has two main parts, a coupling lens 44 and an objective 46. In one embodiment, coupling lens 44 may be customed made in accordance with the present disclosure. Objective 46 may be a 40X, 0.75NA commercial microscope objective.

In the actual setup the laser light may be guided and manipulated by an arrangement of several additional components. The system components may be mounted in adjustable holders and aligned on a precision table. The resulting optical pathway may be bi-directional, as it serves both to deliver the laser light onto the sample and to return the reflected light to the detector, such as a APD.

In practice the confocal endoscope described herein is simple to operate. After turning on the power, the endoscope is brought into contact with the surface of interest. Real-time images may be continuously displayed on the computer monitor, and may be recorded with standard equipment such as a video cassette recorder.

The confocal microscope images at its focal plane, which, in one embodiment, is located 400 $\mu$m from the glass face of the endoscope's microscope objective. The semi-translucent nature of epithelium allows the microscope to image arbitrary planes up to 200 $\mu$m deep into the tissue. Methods for the adjustment of the depth at which the microscope acquires images may include the use of a suction hood attached to the microscope objective to pull the sample, such as an epithelium sample, toward the endoscope. If needed, the hood may also allow a tissue surface to be flushed with a fluid such as water or saline.

FIG. 30 is an overall assembly drawing of an endoscope according to one embodiment. The foundation of the endoscope is its precision bored tube 202 that holds the stack of parts known as the coupling lens 44. In one embodiment, the coupling lens consists of a spacer 204, a index matching reservoir 208, a fiber optic bundle 38, a bundle shield 222, and items that both seal the reservoir and hold the bundle in place (parts 218, 220, 210, and 212). All these parts may be securely held in the tube by the clamping action of the threaded microscope objective 46 and a nut 216.

The lens elements of coupling lens 44 may first glued to their respective mounts with cynoacrylate (4014 wicking-grade medical device adhesive, Loctite Corporation, Rocky Hill, Conn.). Later epoxy (Bipax Tra-Bond BA-F120. Tra-Con, Inc., Medford, Mass.) was applied to the lenses for greater attachment toughness and durability. Positioning of the glass on the metal prior to gluing may be achieved through the use of a milling machine.

In one embodiment, axial positioning may be controlled by the length and squareness of each stacked element. The doublet mount 206 may provide accurate axial spacing between the surrounding elements. Due to tight tolerancing, the optimal axial spacing may be assured without the need to add additional spacers or compensators during assembly.

Radial positioning is a more complex matter, and is principally controlled by the doublet mount 206, which is the only unthreaded part that contacts the tube's inner wall. The index matching reservoir 208 is then naturally aligned with the doublet mount by the singlet lens. The fiber bundle 38 is consequently also naturally aligned with the doublet mount, as long as the hole for the bundle shield 222 was machined within tolerance. In one embodiment, due to the flatness of the doublet lens' left surface, it cannot be relied upon for natural alignment and therefore it must first be centrally glued onto the doublet mount. This provides a precision edge which is used for alignment with the tube (although the fluid reservoir's edge could have been chosen for this purpose instead). The radial alignment of the microscope objective may be dependent on the accuracy of its threads, which is a potential weakness since threads are considered by some experts to be notoriously inaccurate for positioning. The spacer 204 plays no role in radial alignment.

Tilt alignment depends on the squareness of machined edges and threads throughout the assembly, the tilt of lenses when glued, and on the squareness of the nut 216. If the nut is not square, it will force a tilt in the fiber bundle and fluid reservoir, as the natural centering of the singlet lens (the lower lens element of coupling lens 44) allows this unit to swivel like a ball joint in a socket.

In one embodiment, there are five fluid seals on the endoscope: three external seals to keep sanitizing fluid and body fluids from entering the optics, and two internal seals to contain the index fluid. Two of the external seals may consist of Viton O-rings (available from Small Parts, Inc., Miami Lakes, Fla.), a fluorocarbon elastomer that is resistant to many chemicals including liquid silicones like the index fluid, and gluteraldehyde (the sanitizing chemical). The third external seal may be formed by the pipe thread fitting that connects a fiber shield to the endoscope handle.

Figures 31A, 31B:
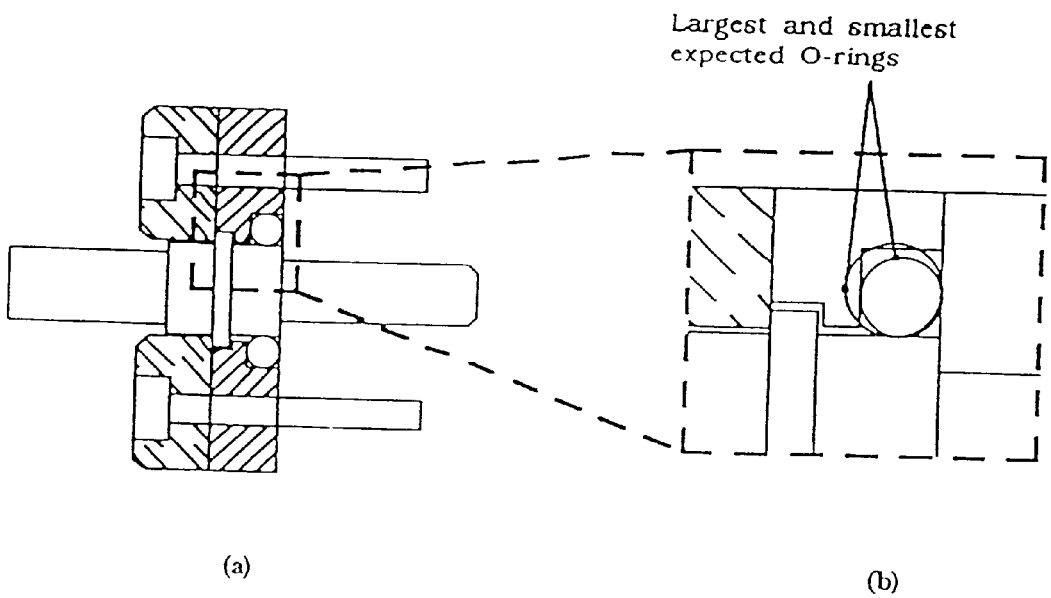
FIG. 31A. shows a lens alignment tool according to one embodiment.
FIG. 31B is a detailed view of an O-ring design according to one embodiment.

In one embodiment, the internal seals are the glues that attach the singlet lens to the reservoir and the small O-ring that surrounds the fiber bundle shield. These seals must not degrade over rime, but they need not be strong. The index fluid exerts only a gravitational pressure on these seals, and pressures due to temperature effects are inconsequential. The O-ring seals against all four of its surrounding surfaces by compression when the clamping screws 220 are tightened. FIG. 31A depicts the mechanical interaction of parts that create this seal. The fiber cap and the O-ring cap were designed as two separate pieces to allow their removal from the fiber bundle. FIG. 31B shows how the variation in O-ring dimension affects its fit and hence the seal. The concern is that extreme sizes, large or small, will not make a good seal. Given a mid-sized O-ring, there is about 0.006 inches of clamping compression, which was deemed sufficient to counteract the fluid's pressure while not stripping the clamping screws' threads.

In one embodiment, this clamped O-ring seal design was found to have a slow leak. Rubber cement was applied over the assembled joint to retain the index fluid, but other embodiments may reduce the volume allotted for seating the O-ring within the O-ring cap to attempt to address the leaking.

The fiber shield 222 may be is an important contributor to the durability of the endoscope, as the fiber bundle may be the most fragile part of the apparatus. The principal threats are that the bundle will be bent too sharply or torqued too far. A fiber shield also needs to be water tight to maintain the endoscope's environmental seal, and should be easily cleanable and sanitizable as well. Alternately, much of the endoscope can be protected from infection by coveting it with a sterile, disposable plastic bag.

The endoscope's fiber shield may be made from a stiff polypropylene tubing and may be attached to the endoscope handle with a hose-barb to pipe thread connector that both prevents bundle torquing and maintains the endoscope seal. This shield discourages sharp bending of the fiber, but a determined effort could still cause a fiber-breaking bend.

Figure 33:
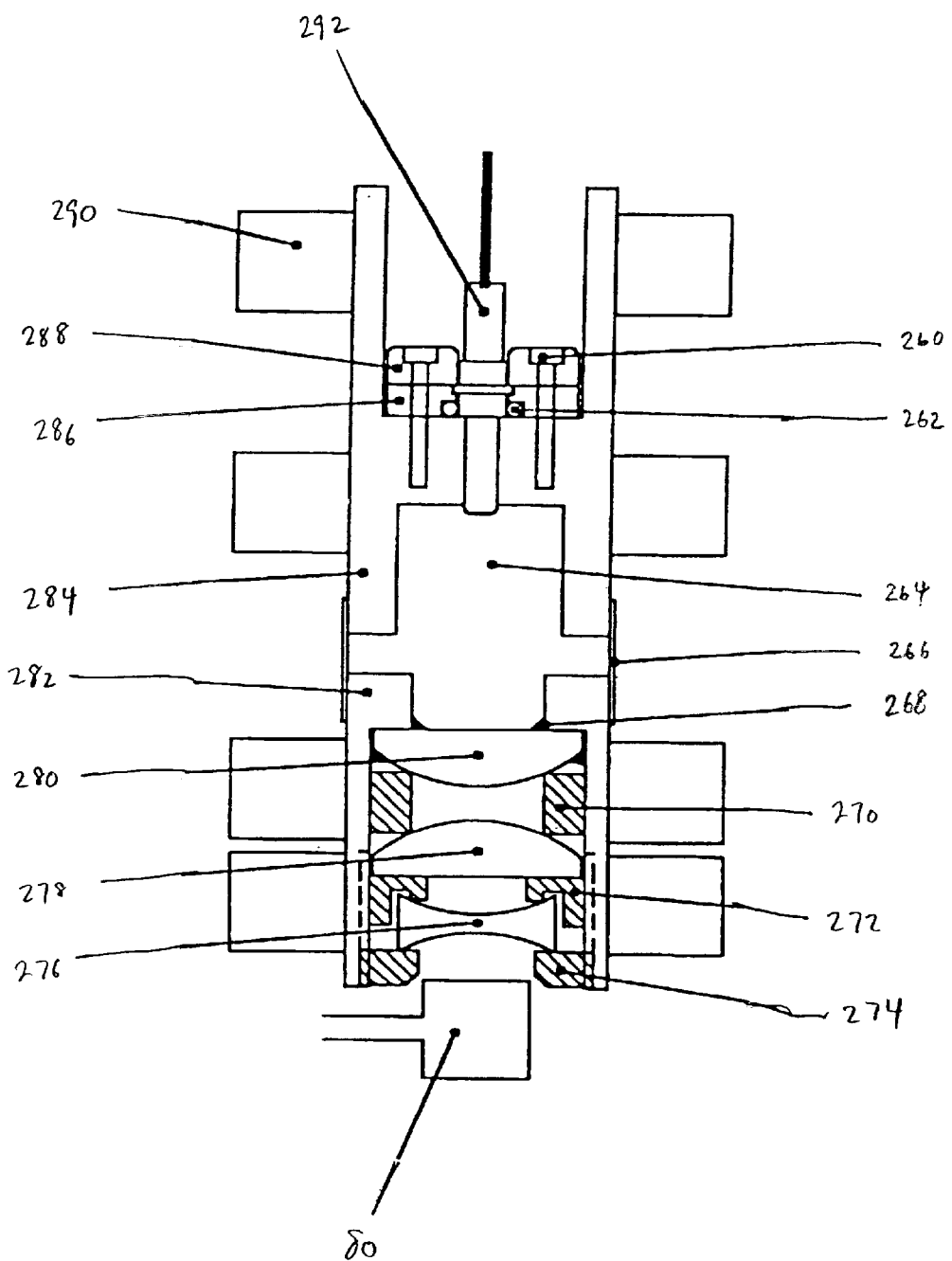
FIG. 33 is one embodiment of a scan lens assembly.

FIG. 33 shows a design of a scan lens 36 and assembly. In this embodiment, the scan lens 36 consists of two tubes (parts 282 and 284) connected by a flexible fluid-filled chamber (parts 264 and 266). The fiber bundle connection and seal use parts that are identical to those on the endoscope.

Face-contacting spacers (parts 270 and 272) provide the alignment for the three lenses (parts 276, 278, and 280). Due to the flat sides of the two lenses, the spacers need to be slip-fit with their tube in order to provide radial alignment.

The index matching reservoir is filled through a tapped hole on the fiber tube (part 284). The reservoir seals (part 268) are syringe-applied household silicone sealant (Dow Corning Corporation, Midland, Mich.). Later the innermost seal was removed, as the acetic acid that silicone produces during curing seemed to be contaminating the index fluid and causing visible inhomogeneities in the index of refraction. As index fluid contamination with dirt and the general cleanliness of lens elements may present a problem, other embodiments may use different cleaning access to the assembled lens.

The flexible coupling may be constructed from material cut from a common Glad sandwich bag, and was attached to the tubes with cable ties. Sealing may be accomplished with Devcon Rubber Adhesive (ITW Brands, Wood Dale, Ill.). This flexible coupling allows the distance between the lens elements and the fiber bundle to be varied.

This flexible coupling is one example of where the positioning accuracy required (less than 0.0005 inch) was too tight to be machined accurately at the inventors' facility, and therefore adjustability was required. Adjustment of this distance was performed by holding the lens tube rigid while using a micrometer-driven stage to position the lens tube. The stage was translated until the spot size reached a minimum, as determined by looking at the distal end of the fiber bundle through a microscope.

In embodiments described herein, a safety interlock may be used to prevent eye damage, wherein the laser could not be turned on unless contact with tissue was assured. Regarding the hazard of electrical shock, shorts in the scan system may have no conductive pathway to the patient if plastic connectors are used to couple the metal fiber shield. In all these cases, the American National Standards Institute (ANSI) publishes guidelines for allowable exposures.

Biocompatible materials may be used with the apparatus described herein, and are important for any temporarily invasive device since tissue contact is impossible to avoid. Additionally, there is a possibility that a part will break off and remain in the patient for an extended period. Metals such as stainless steel and aluminum are nontoxic, but various plastics can be highly toxic. All plastics used should be made from a medical grade polymer to assure their safety. Plastics manufacturers, including Dow, DuPont, and Elf Atochem can supply versions of popular plastics, such as high density polyethylene (HDPE), Pebax, and Hytrel, that are considered safe for endoscope applications and meet FDA specifications.

The endoscope described herein may be disinfected as known in the art. Disinfection is part of the daily usage of an endoscope. The design of the endoscope directly effects how easy and effective cleaning techniques will be. Specific cleaning methods and chemicals must be explicitly planned for. Current good cleaning practices recommend sterilization or at least high-level disinfection ("defined as the inactivation of all vegetative bacteria, mycobacteria, fungi, and viruses, but not necessarily all bacterial endospores" (Martin and Reichelderfer, 1994) for endoscopes that come in contact with mucous membranes or nonintact skin. First the endoscope must be scrubbed thoroughly, especially in any working channels. The disinfection agent can be an alkaline glutaraldehyde bath for 20 min minimum, followed by a sterile water rinse and thorough drying. Additionally, channels should be rinsed with a 70% alcohol solution followed by compressed air to totally dry the device (Martin and Reichelderfer, 1994). The actual practices of hospitals have been reported (Rutala et al., 1991) and should be taken into consideration rather than taken for granted. To facilitate this cleaning, exterior surfaces should be smooth and free from undercuts where bacteria or cleaning fluid might remain after washings.

Ergonomic considerations are important for the endoscope user as well as the patient. The user's primary concern is that the endoscope is easy to handle, position, and hold in place for an extended period. The device's weight, diameter, and handle design play the largest roles here. Minimizing weight makes it easier for the user to hold it for extended times. Reducing the diameter allows for better positioning and observation of spatially constrained cavities. A good handle may improve the user's ability to steadily position the device, and is in addition an obvious indicator of the overall refinement of the ergonomic design. Potential handles include a straight tube like a flashlight, a contoured grip similar to that of a screwdriver, or a pistol grip that allows a more natural wrist position. A successful example of a comfortable and lightweight pistol-style grip can be found on a Fluke 80T-IR Temperature Probe (Fluke Corp., Everett, Wash.). Natural centering is widely recommended as a straightforward and highly accurate method for assuring that multiple lenses will share a common central axis. However, no paper encountered was willing to quantify the absolute accuracy that could reasonably be expected from natural centering. This accuracy is potentially an important piece of information, as the endoscope may have a higher tolerance requirement than many typical optical systems. Both the scan lens and the coupling lens may be designed to use the faces of lens elements to achieve natural centering.

One source (Cade, 1988) warns that natural centering will not work for lenses with a radius greater than 25 or 30 in. (635 or 762 min), and suggests in these cases to instead use the lens' edge for centering. However, the source does not mention how far from the central axis the surface is contacted. This distance has a large effect on the wedging angle and the lens' tendency to center. Another source identifies this wedging angle, or "the net difference in inclination of the front and back lens surfaces at the contact height," (Yoder, 1997) as a primary indicator of whether a lens element will naturally center: a net wedging angle of 17° is the minimum requirement (Yoder, 1997).

Figure 32:
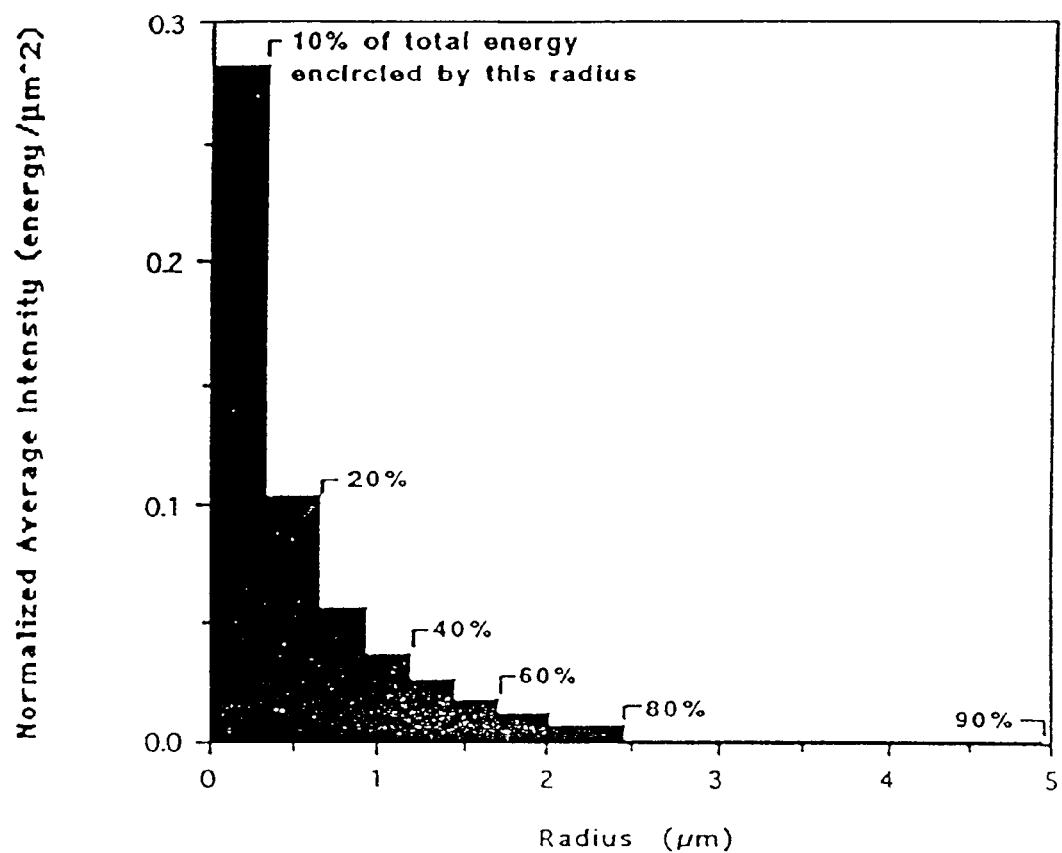
FIG. 32 is a plot of an energy profile according to one embodiment.Detail view of O-ring design.

The scan lens' 36 purpose is to couple the laser into the fiber bundle 38 by focusing, in one embodiment, a 5 mm laser beam into a spot with approximately the same diameter as one of the bundle's fibers. The fibers may be about 5 $\mu$m in diameter, and FIG. 32 is a plot of the spot's expected energy profile, as predicted by the toleranced optical model using the Zemax software. The model predicts that 80% of the focused spot's energy will fall within a 5 $\mu$m diameter circle.

With the benefit of the present disclosure, those of skill in the art will understand that numerous modifications may be made. For instance, in place of the fiber bundle, one may use relay lenses in an articulated arm. Implementation of relay lenses is well known to those of skill in the art. Relay lenses in articulated arms are commonly used to deliver $CO_2$ laser light in surgery and dermatology. The spherical surfaces of the relay lenses may result in significantly less specular reflections than the fiber bundle. In addition, polarization techniques may be used to suppress or reduce specular reflections since the lenses will maintain the polarization of the light unlike the fiber bundle.

Additionally, the scanning system is not required to be a set of orthogonal galvanometers, although galvanometers may allow for higher video rates. Any other device suitable to deflect radiation in the transverse angles to pass over every fiber in the bundle may be used. Possible alternative scanning elements include spinning polygons, acousto-optic cells, and a piezo electric arm.

The number and size of fibers in the bundle may be varied according to need. Several alternatives are available for performing the axial scanning at the distal end of the fiber confocal microscope. These options include: tissue suction (already included), PZT translation, and axial scanning by translation of the distal optics' principal planes. The last technique can be embodied in a set of modifiable optical elements that interact with the microscope objective without changing the objective's focal length and thus magnification. The optical power of the add-on optics may be adjustable. The change in power may result in translation of the front principal plane of the entire distal-optics set. The change in power can be achieved either by advantageously changing the spacing between fixed elements or by means as described in the following paragraphs.

Yet another possibility is a pixellated element capable of changing the index of refraction within each pixel (an example is the Hex Spatial Light Modulator, Meadowlark Optics, Boulder, Colo.).

Those having skill in the art will also understand that confocal imaging may be implemented with several different optical techniques including fluorescence, bright field, reflection, phase contrast, and darkfield imaging.

All of the methods and apparatus disclosed and claimed herein can be made and executed without undue experimentation in light of the present disclosure. While the compositions and methods of this invention have been described in terms of specific embodiments, it will be apparent to those of skill in the art that variations may be applied to the methods and apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,537,472, issued Aug. 27, 1985.

Alfano (ed.), *Fluorescence Spectroscopy for screening and Diagnosis of Cervical Intra-Epithelial Neoplasia.*, San Jose, Calif., *SPIE,* 1995a.

Alfano, Liu, Glassman et al., "Raman spectroscopy as a molecular diagnostic tool for tissues," In: *Advances in Fluorescence Sensing Technology II,* J. Lakowicz, Ed., San Jose, Calif., *SPIE,* 1995b.

Alfano, Tang, Pradham, Lam, Choy, "Fluorescence spectra from cancerous and normal human breast and lung tissues," *IEEE J. Quant. Electron,* vol. QE, pp. 1806–1811, 1987.

American Cancer Society Web Page, "Cancer facts and figures—1997," http://www.cancer.org/97tabp4.html.

Ashfaq, Liang, Saboorian, "Evaluation of PAPNET system for rescreening of negative cervical smears," *Diagnostic Cytopathology,* 13(1):31–6, 1995.

Awen, Hathway, Eddy, Voskuil, Janes, "Efficacy of ThinPrep preparation of cervical smears: a 1,000-case, investigator-sponsored study," *Diagnostic Cytopathology,* 11(1):36–7, 1994.

Baraga, Feld, Rava, "Rapid Near-Infrared raman spectroscopy of human tissue with a spectrograph and CCD detector," *Appl. Spect.,* 46:187–90, 1992.

Baraga, Feld, Rava, "In Situ Optical Histochemistry of Human Artery Using Near Infrared Fourier Transform Raman Spectroscopy," *Proc. Nat. Acad. Sci. USA,* 89:3473–3477, 1992a.

Barer, "Refractometry and interferometry of living cells," *J. Optic. Soc. Amer.,* 47:545–556, 1957.

Bayar, "Mechanical design aspects of optomechanical engineering," *SPIE,* 183:92–100, 1978.

Bayar, "Lens barrel optomechanical design principles," In: *Selected Papers in Optomechanical Design,* D.C. O'Shea, ed., *SPIE,* 770:149–154, 1988.

Beltrame, B Bianco, A Chiabrera, "Automated Analysis of Living Cells through the Quantitative Use of Automated Phase Contrast Microscopy", *Cell Biophy.,* 6:03–116, 1984.

Bereiter-Hahn, Fox, Thorell, "Quantitative Reflection Contrast Microscopy of Living Cells", *J. Cell Biol.,* 82:767–779, 1979.

Bharucha, McCluggage, Lee, Bannister, Kuan, Wilhelm, Nelson, "Grading cervical dysplasia with AgNORs using a semiautomated image analysis system," *Analytical Quantitative Cytology Histology,* 15(5):323–8, 1993.

Bigio, Loree, Mourant et al., "Optical diagnostics based on elastic scattering: recent clinical demonstrations with the Los Alamos optical biopsy system," *SPIE,* 2081:174, 1993.

Bigio, Loree, Mourant, et al., "Noninvasive identification of bladder cancer with sub-surface backscattered light," *SPIE,* 2135:26–31, 1994.

Bigio, Loree, Mourant et al., "Detection of gastrointestinal cancer by elastic scattering and absorption spectroscopies with the Los Alamos optical biopsy system," *SPIE,* 2387:210–217, 1995a.

Bigio, Loree, Mourant, et al, "Spectroscopic diagnosis of bladder cancer with elastic light scattering," *Lasers in Surgery and Medicine,* vol. 16, 1995b.

Biscotti, Hollow, Toddy, Easley, "ThinPrep versus conventional smear cytologic preparations in the analysis of thyroid fine-needle aspiration specimens," *Am. J. Clin. Pathol.,* 104 (2):150–3, 1995.

Boon and Kok, "Neural network processing can provide means to catch errors that slip through human screening of pap smears," *Diag. Cytopathol.,* 9(4):411–6, 1993.

Boon, Kok, Nygaard-Nielsen, Holm, Holund, "Neural network processing of cervical smears can lead to a decrease in diagnostic variability and an increase in screening efficacy: a study of 63 false-negative smears," *Mod. Pathol.,* 7(9):957–61, 1994.

Boone, Kelloff, Steele, "The natural history of intraepithelia neoplasia; relevance to the search for intermediate end-point biomarkers," *J. Cell. Biochem.,* Supp. 16G, pp. 23–26, 1992.

Born and Weft, In: *Principles of Optics,* Pergamon, Oxford, 1975.

Bowan, "Optomechanical design of an endoscope for confocal microscopy," M.S. thesis, University of Texas at Austin, 1997.

Brightman, "Red and white lesions of the oral mucosa," in *Burket's Oral Medicine,* Lynch (ed.), chapter 3, pp. 51–120, Lippincott, 1994.

Brown, In: *Seals and Sealing Handbook,* Oxford: Elsevier Science, 1990.

Brunsting and Mullaney, "Differential light scattering from spherical mammalian cells," *Biophys. J.,* 14:439–53, 1974.

Bur, Knowles, Peko, Corral, Donovan, "Comparison of ThinPrep preparations with conventional cervicovaginal smears, practical considerations," *Acta Cytologica,* 39(4):631–42, 1995.

Cade, "Mounting optical elements," In: *Selected Papers in Optomechanical Design,* D. C. O'Shea, ed., *SPIE,* 770:146–148, 1988.

Carnell et al., "Some experiments on precision lens centering and mounting," In: *Selected Papers in Optomechanical Design,* D.C. O'Shea, ed., *SPIE,* 770:207–219, 1988.

Castleman, *Digital Image Processing,* Prentice-Hall, Englewood Cliffs, N.J., 1979.

Cheong et al., "A review of the optical properties of biological tissues," *IEEE J. Quant. Electron.,* 26(12):2166–85, 1990.

Cheong, "Summary of optical properties," In: *Optical-Thermal Response of Laser-Irradiated Tissue,* A. J. Welch and M. Van Gemert (eds.), chapter 8, pp. 275–301. Plenum, New York, N.Y., 1995.

Coifman, Roklin, Wandzura, "The Fast Multipole Method of the Wave Equation," *IEEE Antennas and Prop.,* 35:7–12, 1993.

Cogswell and Larkin, "The specimen illumination path and its effect on image quality," In: *Handbook of Biological Confocal Microscopy,* J. Pawley (ed.), chapter 8, pp. 127–137, Plenum, New York, N.Y., 2nd edition, 1995.

Cothren et al., "Detection of dysplasia at colonoscopy using laser-induced fluorescence: a blinded study," *Gastrointest. Endosc.,* 44(2):168–176, 1996.

Czernik and Horve, In: *Handbook or Fluid Sealing,* R. V. Brink, ed., New York: McGraw-Hill, 1993.

Delaney and Harris, "Fiberoptics in confocal microscopy," In: *Handbook of Biological Confocal Microscopy,* J. Pawley, Ed,, Plenum, New York, N.Y., 2nd edition, chapter 33, pp. 515–23, 1995.

Delaney et al., "Fibre optic confocal imaging (loci) for subsurface microscopy of the colon in vivo," *J. Anatomy,* 184:157–60, 1994.

Dickensheets and Kino, "A Scanned Optical Fiber Confocal Microscope," *SPIE* 2184:39–47, 1994.

Dunn, "Light scattering properties of cells," Dissertation, The University of Texas at Austin, 1997.

Dunn, Smithpeter, Richards-Kortum, Welch, "Sources of Contrast in Confocal Imaging", *Appl. Optics,* 35:3441–3446, 1996a.

Dunn, Smithpeter, Welch, Richards-Kortum, "Light Scattering From Cells", Optical Society of America Technical Digest—Biomedical Spectroscopy and Diagnostics 50–52, 1996.

Ellison, Maygarden, Novotny, "Quantitative DNA analysis of fresh solid tumors by flow and image cytometric methods: comparison using the Roche pathology workstation image analyzer," *Mod. Pathol.,* 8(3):275–81, 1995.

Fahey, Irwig, Macaskill, "Meta analysis of the pap test accuracy," *Am. J. Epidemiol.,* 141:680–689, 1995.

Feld et al., *An integrated System/or Spectral Diagnosis, Guidance, and Ablation in Laser Angiosurgery.,* pp. 189–202., Mosby-Year Book, 1993.

Feld, Kramer, Albagli et al., "LAS II: An Integrated System for Spectral Diagnosis, Guidance, and Ablation in Laser Angiosurgery," In: *The Practice of Interventional Cardiology,* 2nd ed., J. H. K. Vogel SBK, eds., St. Louis: Mosby-Year Book, 189–202, 1993.

Fischler and Toddy, "Nongynecologic cytology utilizing the Thin-Prep processor," *Acta Cytologica,* 40(4):669–75, 1996.

Gere and Timoshenko, In. *Mechanics of Materials,* Boston: PWS-KENT, 2nd ed., 1984.

Giniunas et al., "Scanning fiber-optic microscope for microendoscopy with gradient index lenses probe," In: *Optical Fibers in Medicine VIII.,* vol. 1893 of *Optical Fiber in Medicine VIII,* pp. 90–2, SPIE Proc., 1993a.

Giniunas, Juskaitis, Shatalin, "Endoscope with optical sectioning capability," *Appl. Optics,* 32(16):2888–90, 1993b.

Gmitro and Aziz, "Confocal microscopy through a fiber optic imaging bundle," *Optics Lett.,* 18(8):565–7, 1993.

Gourgouliatos, Welch, Diller, "Microscopic instrumentation and analysis of laser-tissue interaction in a skin flap model," *Transactions of the ASME,* 302:301–7, 1991.

Gu, Sheppard, Gan, "Image formation in a fiber-optical confocal scanning microscope," *Optical Society of America,* 8(11):1755–61, 1991.

Ham and Cormack, Histology, J. B. Lippincott Co., 8th edition, 1979.

Hecht, *Optics,* Addison-Wesley, 2nd edition, 1987.

Hoda, Saccomanno, Schreiber, Decker, Koss, "Automated sputum screening with PAPNET system: a study of 122 cases," *Human Pathology,* 27(7):656–9, 1996.

Hopkins, "Some thoughts on lens mounting," In: *Selected Papers in Optomechanical Design,* D. C. O'Shea, ed., SPIE, 770:174–176, 1988.

Horne, In: *Optical Production Technology,* London: Adam Hilger, 1972.

Huang, Swanson, Lin, et al., "Optical coherence tomography," *Science,* 254:1178–81, 1991.

Hung, Lam, LeRiche, Palcic, "Autofluorescence of normal and malignant bronchial tissue," *Las. Surg. Med.,* 11:99–105, 1991.

Hutchinson, Agarwal, Denault, Berger, Cibas, "A new look at cervical cytology. ThinPrep multicenter trial results," *Acta Cytologica,* 36(4):490–504, 1992.

Hutchinson, Isenstei, Goodman, Hurley, Douglass, Mui, Patten, Zahniser, "Homogeneous sampling accounts for the increased diagnostic accuracy using the ThinPrep processor," *Am. J. Clin. Path.,* 101(2):215–9, 1994.

Inoue, "Foundations of confocal scanned imaging in light microscopy," In: *Handbook of Biological Confocal Microscopy,* J. Pawley, Ed., Plenum, New York, N.Y., 2nd edition, pp- 1–17, 1995.

Izatt, Hee, Owen, "Optical coherence microscopy in scattering media," *Optics Lett.,* 19(8):590–2, 1994.

Jester et al., "In vivo, real-time confocal imaging," *J. Electron Microscopy Tech.,* 18:50–60, 1991.

Juskaitis et al., "Real time white light reflection confocal microscopy using a fiber optic bundle," *Scanning* 19(1):15–19, 1997.

Keller, "Objective lenses for confocal microscopy," In: *Handbook of Biological Confocal Microscopy,* James Pawley, (ed.), chapter 7, pp. 77–86, Plenum, 1989.

Kempe, Rudolph, Welsch, "Comparative study of confocal and heterodyne microscopy for imaging through scattering media," *J. Optic. Soc. Am. A,* 13(1):46–52, 1996.

Kimura and Wilson, "Confocal scanning optical microscopy using single mode fiber for signal detection," *Appl. Optics,* 30(16):2143–50, 1991.

Kimura and Wilson, "Effect of axial pinhole displacement, in confocal microscopes," *Appl. Optics,* 32(13):2257–61, 1993.

Koss, Lin, Schreiber, Elgert, Mango, "Evaluation of the PAPNET cytologic screening system for quality control of cervical smears," *Am. J. Clin. Path.,* 101(2):220–9, 1994.

Kurman, Henson, Herbst, Noller, Schiffman, "Interim Guidelines for Management of Abnormal Cervical Cytology," *J. Am. Med. Assoc.,* 271:11866–1869, 1994.

Larsen, "Invasive Cervical Cancer Rising in Young White Females (News)," *J. Nat. Cancer Inst.,* 86:6–7, 1994.

Leuing et al., "Fluorescence imaging and spectroscopy of 5-aminolevulinic acid induced protoporphyirn IX for the detection of neoplastic lesion in the oral cavity," *Am. J. Surg.,* 172:674–77, 1996.

Liu, Beauvoit, Kimura, Chance, "Dependence of tissue optical properties on solute-induced changes in refractive index and osmolarity" *J. Biomed. Optics,* 1:200–210, 1996.

Loney, "Scanner component and head development for confocal microscopy using moving mirror technology," In: *Recording Systems,* 1987:129–36 (vol. 1987), *SPIE,* 21–23, 1993.

Mahadevan, Mitchell, Silva, Thomsen, Richards-Kortum, *Las. Surg. Med.,* 13:647–655, 1993.

Mahadevan-Jansen and Richards-Kortum, "Raman spectroscopy for the detection of cancers and pre-cancers (review), *J. Biomed. Opt,* 1:31–70, 1996.

Maier, Walker, Fantini, Franceschini, Gratton, "Possible correlation between blood glucose concentration and the reduced scattering coefficient of tissues in the near infrared," *Optics Lett.,* 19:2062–2064, 1994.

Mango, "Computer-assisted cervical cancer screening using neural networks," *Cancer Lett.,* 77(2–3):155–62, 1994.

Mango, Kelly, Paull, Ludin, Copeland, Solomon, Schiffman, Sherman, "PAPNET analysis of reportedly negative smears preceding the diagnosis of a high-grade squamous intraepithelial lesion or carcinoma," *Mod. Path.,* 7(5):578–81, 1994.

Manoharan, Baraga, Feld, "Quantitative Histochemical Analysis of Human Artery Using Raman Spectroscopy," *Photochem. Photobiol.,* 16:211, 1992.

Manoharan, Wang, Dasari, "Ultraviolet resonance raman spectroscopy for detection of colon cancer," *Las. Lif. Sci.,* 1994.

Marieb, *Human Anatomy and Physiology,* Benjamin/Cummings, Redwood City, Calif., 2nd edition, 1992.

Martin and Reichelderfer, APIC guideline for infection prevention and control in flexible endoscopy, "*Amer. J. Infect. Control,* 22:19–38, 1994.

Massig et al., "Real-time confocal laser scan microscope for examination and diagnosis of the eye in vivo," Appl. Optics, 33(4):690–4, 1994.

Masters and Thaer, "Real-time scanning slit confocal microscopy of the in vivo human cornea," *Appl. Optics,* 33(4):695–701, 1994.

McGoogan and Reith, "Would monolayers provide more representative samples and improved preparations for cervical screening? overview and evaluation of systems available," *Acta Cytologica,* 40(1):107–19, 1996.

Meyer and Gerson, "A comparison of human palatal and buccal mucosa," *Periodontics,* 2(1):284–91, 1964.

Miller, "Evaluation of the Impact of Screening for Cancer of Cervix," In: *Screening for Cancer of the Uterine Cervix,"* Hakama M, A. B. M, Day NE, ed., New York: Oxford University Press, 1986.

Mitchell, "The accuracy of colposcopy," *Clin. Consult. Obstet. Gynecol.,* 6:70–73, 1994.

Noble, "Some parameter measurements," In: *Optical Shop Testing*, D. Malacara, ed., New York: John Wiley and Sons, 16:459–478, 1978.

Ouwerkerk-Noordam, Boon, Beck, "Computer-assisted primary screening of cervical smears using the PAPNET method: comparison with conventional screening and evaluation of the role of the cytologist.," *Cytopathology*, 5(4):211–8, 1994.

Ozzello, In: *The Breast*, Williams and Williams, Baltimore, 1984.

Parkin, Pisani, Ferlay, "Estimates of the Worldwide Incidence of Eighteen Major Cancers in 1985," *Int. J. Cancer*, 54:594–606, 1993.

Perez-Reyes, Mulford, Rutkowski, Logan-Young, Dawson, "Breast fine-needle aspiration, a comparison of thin-layer and conventional preparation," *Amer. J Clin. Path.*, 102 (3):349–53, 1994.

Petroll, Cavanagh, Jester, "Three-dimensional imaging of corneal cells using in vivo confocal microscopy," *J. Micros.*, 170(3):213–9, 1993.

Prahl, Van Gemert, Welch, "Determining the optical properties of turbid media by using the adding-doubling method," *Appl. Optics*, 32:559–568, 1993.

Prasankumar and Gopinath, Senior project for EE464H7, University of Texas-Austin, 1997.

Pugh, In: *Total Design*, Wokingham, England: Addison-Wesley, 1990.

Rajadhyaksha et al., "Video-rate confocal scanning laser microscope for in vivo imaging of human skin.," San Diego, CS, Annual Meeting of ASLMS, 1995a.

Rajadhyaksha, Grossman, Esterowitz, Webb, Anderson, "In vivo confocal scanning laser microscopy of human skin: Melanin provides strong contrast," *J. Invest. Dermatol.*, 104(6):946–52, 1995b.

Ramanujam, Mitchell, Mahadevan et al., *Lasers Surg. Med.*, 1996b.

Ramanujam, Mitchell, Mahadevan, et al., "Development of a multivariate statistical algorithm to analyze human cervical tissue fluorescence acquired in vivo," *Lasers Surg. Med.*, 19(1):46–62, 1996c.

Ramanujam, Mitchell, Mahadevan, Thomsen, Silva, Richards-Kortum, "In vivo diagnosis of cervical intraepithelial neoplasia using 337 nm laser induced fluorescence," In: *Proc. Nat. Acad. Sci. USA*, 91:10193–97, 1994a.

Ramanujam, Mitchell, Mahadevan, Thomsen, Silva, Richards-Kortum, *Gynecol. Oncol.*, 52:31–38, 1994b.

Reavell and Welford, "Precision construction of optical systems," In: *Selected Papers in Optomechanical Design*, D. C. O'Shea, ed., *SPIE*, 770:220–222, 1988.

Reiss, "Opto-mechanical instrument design," In: *Optomechanical Systems Engineering*, D. Vukobratovich, ed., *SPIE*, 817:154–170, 1987.

Richards-Kortum, Rava, Petras, Fitzmaurice, Sivak, Feld, "Spectroscopic diagnosis of colonic dysplasia," *Photochem. Photobiol.*, 53(6):777–786, 1991.

Richards-Kortum, Durkin, Zeng, "Description and Performance of a fiber optic confocal fluorescence spectrometer," *Appl. Spectroscopy*, 48:350–5, 1994.

Richards-Kortum, *Role of Laser Induced Fluorescence Spectroscopy in Diagnostic Medicine*, chapter 21, Plenum, 1994.

Richards-Kortum, Ramanujam, Yazdi et al., Fluorescence Spectroscopy for Screening and Diagnosis of Cervical Intra-Epithelial Neoplasia. In: *Advances in Laser and Light Spectroscopy to Diagnose Cancer and Other Diseases II*, Alfano R R, ed., San Jose, Calif.: *SPIE*, 1995a.

Richards-Kortum, Maadevan, Mitchell, Ramanujam, Malpica, Thomsen, "Optical Techniques for Diagnosis of Cervical Precancer: A Comparison of Raman and Fluorescence Microscopy," In: *Advances in Fluorescence Sensing Technology II*, Lakowicz JR, ed., San Jose, Calif.: *SPIE*, 1995b.

Rosenthal, Acosta, Peters, "Computer-assisted rescreening of clinically important false negative cervical smears using the PAPNET testing system," *Acta Cytologica*, 40(1):120–6, 1996.

Rutala et al., "Disinfection practices for endoscopes and other semicritical items," *Infection Control and Hospital Epidemiology*, 12:282–288, 1991.

Ryan, Stastny, Remmers, Pedigo, Cahill, Frable, "PAPNET-directed rescreening of cervicovaginal smears: a study of 101 cases of atypical squamous cells of undetermined significance," *Am. J. Clin. Path.*, 105(6):711–8, 1996.

Sasian, "Design, assembly, and testing of an objective lens for a free-space photonic switching system," *Optical Engineering*, 32(8):1871–1878, 1993.

Sawyer, "Contact stresses and their optical effects in biconvex optical elements," In: *Optomechanical and Precision Instrument Design*, A. E. Hatheway, ed., *SPIE*, 2542:58–69, 1995.

Schmitt et al, "Optical characterization of dense tissues using low-coherence interferometry," *SPIE*, 1889:197–210, 1993.

Schmitt, Knuttel, Yadlowsky, "Confocal Microscopy in Turbid media," *J. Optic. Soc. Am. A*, 11(1):2226–35, 1994a.

Schmitt, Knuttel, Yadlowsky, Eckhaus, "Optical-coherence tomography of a dense tissue: statistics of attenuation and backscattering," *Phys. Med. Biol.*, 39:1705–20, 1994.

Schomacker, Frisoli, Compton et al., "Laser-Induced fluorescence of colonic tissue: Basic biology and diagnostic potential," *Las. Surg. Med.*, 12:63–78, 1992.

Shafer, Hine, Barnet, Levy, *A textbook of oral pathology*, W. B. Saunders, 4th edition, 1983.

Sheppard and Cogswell, "Effects of aberrating layers and tube length on confocal imaging properties," *Optik*, 87(1):34–38, 1991.

Sheppard and Gu, "Axial imaging through an aberrating layer of water in confocal microscopy," *Optics Communications*, 88:180–190, 1992.

Sheppard, Gu, Brain, Zhou, "Influence of spherical aberration on axial imaging of confocal reflection microscopy," *Appl. Optics*, 33(4):616–24, 1994.

Sherman, Mango, Kelly, Paull, Ludin, Copeland, Solomon, Schiffman, "PAPNET analysis of reportedly negative smears preceding the diagnosis of a high-grade squamous intraepithelial lesion or carcinoma," *Mod. Pathol.*, 7(5):578–81, 1994.

Slagel, Zaleski, Cohen, "Efficacy of automated cervical cytology screening," *Diagnostic Cytopathology*, 13(1):26–30, 1995.

Smith, *Modern Optical Engineering*, McGraw-Hill, N.Y., 2nd edition, 1990.

Smith, *Modern Lens Design*, McGraw-Hill, N.Y., 1992.

*SPIE Proceedings*, "Mode Locked Solid State Laser Sources for Optical Coherence Tomography," vol. 2981, San Jose, Calif., 1997.

Stelzer, "Designing a confocal fluorescence microscope," In: *Multidimensional Microscopy*, P. C. Cheng et al. (eds.), chapter 2, pp. 33–45. Springer-Verlag, 1994.

Swanson et al., "In vivo retinal imaging by optical coherence tomography," *Optics Lett.*, 18(21):1864–66, 1993.

Tezuka, Oikawa, Shuki, Higashiiwai, "Diagnostic efficacy and validity of the ThinPrep method in cervical cytology," *Acta Cytologica*, 40(3):513–8, 1996.

Thorburn, "Concepts and misconceptions in the design and fabrication of optical assemblies," In: *Optomechanical Systems Design,* M. Bayar, ed., *SPIE,* 250:2–7, 1980.

Tsay and Pozar, "Application of the FDTD Technique to Periodic Problems in Scatterina and Radiation," *IEEE Microwave Guided Wave Lett.,* 3:250–252, 1993.

Van de Hulst, In: *Light Scattering by Small Particles,* Dover, N.Y., 1957.

Vo-Dinh, Panjehpour, Overholt, Farris, Buckley, Sneed, "In vivo cancer diagnosis of the esophagus using differential normalized fluorescence (DNF) indices," *Las. Surg. Med.,* 16:41–47, 1995.

Vuong, Vacher-Lavenu, Marsan, Baviera, "[computer-assisted rescreening of cervicovaginal smears stained by the papanicolaou method, evaluation of the PAPNET system apropos of 225 cases]," [*French*] *Archives d Anatomie et de Cytologie Pathologiques,* 43(3):147–53, 1995.

Webb, "Optics for later rasters," *Appl. Optics,* 23(20):3680–3, 15, 1984.

Webb, "The Pixilated Image," In: *Handbook of Biological Confocal Microscopy.* (J. Pawley, ed.), ch. 7, pp. 77–86, Plenum, N.Y., 1989.

Webb and Dorey, "The pixilated image," In: *Handbook of Biological Confocal Microscopy,* (J. Pawley, Ed.), chapter 4, pp. 55–67, Plenum, N.Y., 1995.

Webb and Hughes, "Scanning laser opthalmoscope," *IEEE Transactions on Biomedical Engineering,* 28:488–492, 1981.

Webb and Hughes, "Detectors for scanning video imagers," *Appl. Optics,* 32(31):6227–35, 1993.

Webb, Hughes, Delori, "Confocal scanning laser opthalmoscope," *Appl. Optics,* 26:1492–99, 1987.

Westort, "Design and fabrication of high performance relay lenses," In: *Selected Papers in Optomechanical Design,* D. C. O'Shea, ed., *SPIE,* 770:199–206, 1988.

Wilbur, Cibas, Merritt, James, Berger, Bonfiglio, "ThinPrep processor. clinical trials demonstrate an increased detection rate of abnormal cervical cytologic specimens," *Am. J. Clin. Path.,* 101(2):209–14, 1994.

Wilson, "The role of the pinhole in confocal imaging systems," In: *Confocal Microscopy Handbook* (J. B. Pawley, ed.), pp. 99–113, 1995.

Wilson, "The role of the pinhole in confocal imaging systems," In: *Handbook of Biological Confocal Microscopy* (J. B. Pawley, ed.), ch. 11, pp. 167–182, Plenum Press, 2nd ed., 1995.

Wilson and Carlini, "Size of the detector in confocal imaging systems," *Optics Lett.,* 12 (4):227–9, 1987.

Wilson and Carlini, "Effect of detector displacement in confocal imaging systems," *Appl. Optics,* 27(18):3791–98, 1988.

Wray and Lai-Goldman, "The design and use of a computer-based digital image acquisition, management, and communications system for conferencing in pathology," *Archives d Anatomic et de Cytologie Pathologiques,* 43(4):271–4, 1995.

Yadlowsky, Schmitt, Bonner, "Multiple scattering effects in optical coherence microscopy.," *Appl. Optics,* 34(25):5699–5707, 1995.

Yee, "Numerical Solutions of Initial Boundary Value Problems Involving Maxwell's Equations in Isotropic Media", *IEEE Transactions on Antennas and Propagation,* AP-14, 302–307, 1966.

Yoder Jr., In: *Opto-Mechanical Systems Design,* New York: Marcel Dekker, 1993.

Yoder Jr., "Optical mounts: lenses, windows, small mirrors, and prisms," In: *Handbook of Optomechanical Engineering,* A. Ahmad. ed., Boca Raton: CRC, 6:151–210, 1997.

What is claimed is:

1. A confocal imaging apparatus for analyzing a sample, comprising:
   a radiation source configured to emit incident radiation;
   a scan system in optical communication with said radiation source and configured to controllably deflect said incident radiation;
   a scan lens in optical communication with said scan system and configured to focus said incident radiation;
   a plurality of fibers having a proximate end and a distal end, said proximate end in optical communication with said scan lens and configured to receive said incident radiation focused from said scan lens;
   a proximal index matching agent coupled to said proximate end and configured to reduce specular reflection from said plurality of fibers;
   a distal index matching agent coupled to said distal end and configured to reduce specular reflection from said plurality of fibers;
   a coupling lens in optical communication with said distal end and configured to focus said incident radiation toward said sample to produce secondary radiation from said sample;
   a variable-strength suction agent adjacent to said distal end and configured to adjust a focal plane of said sample by increasing or decreasing an amount of suction; and
   a detector in optical communication with said scan system and configured to receive at least a portion of said secondary radiation and to produce a signal corresponding therewith.

2. The apparatus of claim 1, wherein said incident radiation comprises near infrared radiation.

3. The apparatus of claim 1, wherein said radiation source comprises a Ti:Sapphire laser.

4. The apparatus of claim 1, wherein said radiation source comprises a diode pumped Nd:YAG laser.

5. The apparatus of claim 1, wherein said scan system comprises a pair of orthogonal galvanometers.

6. The apparatus of claim 1, wherein said scan system comprises a spinning polygon.

7. The apparatus of claim 1, wherein said scan system and said scan lens are adapted to illuminate a single fiber of said plurality of fibers.

8. The apparatus of claim 1, further comprising a depth translation system in operative relation with said plurality of fibers, the system comprising a translation stage.

9. The apparatus of claim 1, wherein said suction agent comprises a tube having a plurality of channels, wherein at least one of said channels is adapted to deliver saline, and wherein at least one of said channels is adapted for suction.

10. The apparatus of claim 1, wherein centers of said plurality of fibers are separated by about 5 microns.

11. The apparatus of claim 1, wherein at least one of said plurality of fibers comprises a core and a cladding, and wherein said distal index matching agent comprises a fluid having an index of refraction substantially equal to an index of refraction of said core.

12. The apparatus of claim 1, further comprising a beam splitter in optical communication with said radiation source and said detector, said beam splitter comprising a wedge angle.

13. The apparatus of claim 1, wherein said scan system is configured to controllably deflect said incident radiation in a raster pattern.

14. The apparatus of claim 1, further comprising an aperture positioned between said coupling lens and said detector.

15. The apparatus of claim 14, wherein one of said plurality of fibers is an illuminated fiber transporting said secondary radiation toward said detector, and wherein said aperture has a diameter adapted to block at least a portion of said secondary radiation emanating from a proximate end of one or more fibers adjacent said illuminated fiber.

16. The apparatus of claim 1, further comprising a controller coupled to said scan system and to said detector.

17. The apparatus of claim 16, further comprising control electronics and a video card coupled to said controller, said control electronics adapted to provide one or more timing signals to said video card.

18. The apparatus of claim 1, further comprising an objective in optical communication with said coupling lens, and wherein a magnification of said coupling lens is adapted to fill said objective with said incident radiation.

19. The apparatus of claim 1, wherein said apparatus has a lateral resolution of about 5 microns.

20. A confocal imaging apparatus for analyzing a sample, comprising:
    a laser configured to emit incident radiation;
    a scan system in optical communication with said laser and configured to controllably deflect said incident radiation in a raster pattern;
    a scan lens in optical communication with said scan system and configured to focus said incident radiation in said raster pattern;
    a plurality of fibers having a proximate end and a distal end, said proximate end in optical communication with said scan lens and configured to receive said incident radiation focused from said scan lens in said raster pattern;
    a proximal index matching agent coupled to said proximate end and configured to reduce specular reflection from said plurality of fibers;
    a distal index matching agent coupled to said distal end and configured to reduce specular reflection from said plurality of fibers;
    a coupling lens in optical communication with said distal end and configured to focus said incident radiation in said raster pattern toward said sample to produce secondary radiation from said sample;
    a variable-strength suction agent adjacent to said distal end and configured to adjust a focal plane of said sample by increasing or decreasing an amount of suction; and
    a detector in optical communication with said scan system and configured to receive at least a portion of said secondary radiation and to produce a signal corresponding therewith.

21. The apparatus of claim 20, wherein at least one of said plurality of fibers comprises a core and a cladding, and wherein said distal index matching agent comprises a fluid having an index of refraction substantially equal to an index of refraction of said core.

22. The apparatus of claim 20, wherein at least one of said plurality of fibers comprises a core and a cladding, and wherein said proximal index matching agent comprises a fluid having an index of refraction between an index of refraction of said core and an index of refraction of said cladding.

23. The apparatus of claim 22, wherein said fluid has an index of refraction of about halfway between said index of refraction of said core and said index of refraction of said cladding.

24. The apparatus of claim 20, further comprising a depth translation system in operative relation with said plurality of fibers, the system comprising a translation stage.

25. The apparatus of claim 20, further comprising a controller coupled to said scan system and to said detector.

26. An endoscopic confocal imaging apparatus for in vivo analysis of a sample, comprising:
    a confocal system comprising:
    a radiation source configured to emit incident radiation;
    a scan system in optical communication with said laser and configured to controllably deflect said incident radiation;
    a scan lens in optical communication with said scan system and configured to focus said incident radiation;
    a plurality of fibers having a proximate end and a distal end, said proximate end in optical communication with said scan lens and configured to receive said incident radiation focused from said scan lens;
    a detector in optical communication with said scan system; and
    an endoscope comprising:
    a proximal index matching fluid reservoir configured to sealably contain a proximal index matching fluid, said reservoir being coupled to said proximal end, and said fluid being configured to reduce specular reflection from said plurality of fibers;
    a distal index matching fluid reservoir configured to sealably contain a distal index matching fluid, said reservoir being coupled to said distal end, and said fluid being configured to reduce specular reflection from said plurality of fibers;
    a coupling lens in optical communication with said distal end and configured to focus said incident radiation toward said sample to produce secondary radiation from said sample detectable by said detector to produce a signal corresponding therewith;
    a variable-strength suction agent adjacent to said distal end and configured to adjust a focal plane of said sample by increasing or decreasing an amount of suction; and
    an endoscopic tube configured to house said distal end, said reservoir, said coupling lens, and said suction agent.

27. The apparatus of claim 26, further comprising an objective in optical communication with said coupling lens, and wherein a magnification of said coupling lens is adapted to fill said objective with said incident radiation.

28. The apparatus of claim 26, further comprising a fiber shield configured to house and protect at least a portion of said plurality of fibers.

29. The apparatus of claim 26, wherein said scan system is configured to controllably deflect said incident radiation in a raster pattern.

30. The apparatus of claim 26, further comprising a controller coupled to said scan system and to said detector.

31. A method for confocal imaging of a sample, comprising:
    emitting incident radiation from a radiation source;
    controllably deflecting said incident radiation with a scan system in optical communication with said radiation source;
    focusing said incident radiation with a scan lens in optical communication with said scan system;
    receiving said incident radiation focused from said scan lens with a proximate end of a plurality of fibers, said proximate end in optical communication with said scan lens;

reducing specular reflection from said plurality of fibers with a proximal index matching agent coupled to a proximal end of said plurality of fibers;

reducing specular reflection from said plurality of fibers with a distal index matching agent coupled to a distal end of said plurality of fibers;

focusing said incident radiation toward said sample to produce secondary radiation from said sample with a coupling lens in optical communication with said distal end;

adjusting a focal plane of said sample by increasing or decreasing an amount of suction from a variable-strength suction agent adjacent to said distal end of said plurality of fibers;

receiving said secondary radiation focused from said coupling lens with said distal end;

focusing said secondary radiation through said scan system with said scan lens;

detecting at least a portion of said secondary radiation with a detector in optical communication with said scan system; and producing a signal corresponding to said secondary radiation detected by said detector to image said sample.

32. The method of claim 31, wherein said coupling lens, said distal end, said distal index matching agent, said proximal index matching agent, and said variable-strength suction agent comprise an endoscope, and wherein said imaging of said sample comprises in vivo endoscopic imaging of said sample.

33. The method of claim 31, wherein said controllably deflecting said incident radiation comprises deflecting said incident radiation in a raster pattern.

34. The method of claim 31, wherein said sample comprises biological tissue.

35. The method of claim 31, wherein said sample comprises an integrated circuit wafer, or portion thereof.

36. The method of claim 31, further comprising enhancing contrast of said sample with a contrast agent.

37. The method of claim 36, wherein said contrast agent comprises 5-aminolevulinic acid.

38. The method of claim 36, wherein said contrast agent comprises acetic acid.

39. The method of claim 38, wherein said acetic acid consists of about 6% acetic acid.

40. The method of claim 31, further comprising modifying a focus depth with a depth translation system in operative relation with said plurality of fibers, the system comprising a translation stage.

41. The method of claim 31, wherein said imaging comprises cross sectional imaging.

* * * * *

UNITED STATES PATENT AND TRADEMARK OFFICE
CERTIFICATE OF CORRECTION

PATENT NO. : 6,370,422 B1
DATED : April 9, 2002
INVENTOR(S) : Richards-Kortum et al.

It is certified that error appears in the above-identified patent and that said Letters Patent is hereby corrected as shown below:

<u>Title page,</u>
Item [75], please delete "Palo Alto, TX" and insert -- Palo Alto, CA -- therefor.

Signed and Sealed this

Tenth Day of September, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,370,422 B1 | Page 1 of 1 |
| APPLICATION NO. | : 09/272719 | |
| DATED | : April 9, 2002 | |
| INVENTOR(S) | : Rebecca R. Richards-Kortum et al. | |

It is certified that error appears in the above-identified patent and that said Letters Patent is hereby corrected as shown below:

In the Specification

Column 1, at line 10, replace the entire paragraph with the following paragraph:

This invention was made with government support under Grant no. CA073920 awarded by the National Institutes of Health; and Grant no. 9253612 awarded by the National Science Foundation. The government has certain rights in the invention.

Signed and Sealed this
Twenty-first Day of April, 2015

Michelle K. Lee
*Director of the United States Patent and Trademark Office*